US010124056B2

(12) United States Patent
Milner et al.

(10) Patent No.: US 10,124,056 B2
(45) Date of Patent: Nov. 13, 2018

(54) ALKYLATED INFLUENZA VACCINES

(71) Applicant: SANOFI PASTEUR INC., Swiftwater, PA (US)

(72) Inventors: Brooke S. Milner, Easton, PA (US); Jonathan Haines, Effort, PA (US); Steven L. Hauser, Easton, PA (US); Janet Beebe Poli, Bethlehem, PA (US)

(73) Assignee: Sanofi Pasteur Inc., Swiftwater, PA (US)

( * ) Notice: Subject to any disclaimer, the term of this patent is extended or adjusted under 35 U.S.C. 154(b) by 0 days.

(21) Appl. No.: 14/829,158

(22) Filed: Aug. 18, 2015

(65) Prior Publication Data
US 2016/0045590 A1    Feb. 18, 2016

Related U.S. Application Data

(60) Provisional application No. 62/038,753, filed on Aug. 18, 2014.

(51) Int. Cl.
*A61K 39/145* (2006.01)
*A61K 39/00* (2006.01)
*A61K 39/12* (2006.01)
*C12N 7/00* (2006.01)
*C12N 7/02* (2006.01)

(52) U.S. Cl.
CPC ............ *A61K 39/145* (2013.01); *C12N 7/00* (2013.01); *A61K 2039/5252* (2013.01); *A61K 2039/70* (2013.01); *C12N 2760/16034* (2013.01); *C12N 2760/16063* (2013.01)

(58) Field of Classification Search
CPC .......... A61K 2039/5252; A61K 39/145; A61K 2039/70; C12N 2760/16034; C12N 7/00
See application file for complete search history.

(56) References Cited

U.S. PATENT DOCUMENTS 7,638,608 B2 * 12/2009 Kapteyn ............. C07K 14/005
424/184.1

FOREIGN PATENT DOCUMENTS

| EP | 1420065 A1 | 5/2004 |
|---|---|---|
| EP | 1481985 A1 | 12/2004 |
| JP | 62221636 A | 9/1987 |
| WO | 2011/138229 A1 | 11/2011 |
| WO | 2011/154976 A2 | 12/2011 |

OTHER PUBLICATIONS

Hickey et al., Pharmaceutical Biotechnology, 2014, 103:821-827.*
She et al., Proteomics, 2013, 13:3537-3547.*
Cox et al., Biologicals, 2009, 37:182-189.*
CDC, 1996, CDC MMWR Recommendations and Reports, 45(RR-12): pdf pp. 1-18).*
Nestorowicz et al., Molecular Immunology, 1985, 22(2):145-154.*
Hickey, J. et al., Mechanism of a Decrease in Potency for the Recombinant Influenza A Virus Hemagglutinin H3 Antigen During Storage, Journal of Pharmaceutical Sciences, 103(3):821-827 (2014).
Holtz, K. et al., Modifications of cysteine residues in the transmembrane and cytoplasmic domains of a recombinant hemagglutinin protein prevent cross-linked multimer formation and potency loss, BMC Biotechnology, 14(1):20 pages (2014).
International Search Report for PCT/US2015/045689, 5 pages (dated Nov. 26, 2015).
Jackson, D. et al., Antigenic Determinants of Influenza Virus Hemagglutinin, Virology, 89(1):199-205 (1978).
Nestorowicz, A. et al., Antibodies elicited by influenza virus hemagglutinin fail to bind to synthetic peptides representing putative antigenic sites, Molecular Immunology, 22(2):145-154 (1985).
Wang, T. et al., Vaccination with a synthetic peptide from the influenza virus hemagglutinin provides protection against distinct viral subtypes, Proceeds of the National Academy of Sciences USA, 107(44):18979-18984 (2010).
Written Opinion for PCT/US2015/045689, 8 pages (dated Nov. 26, 2015).
Gapta, P. et al., "Inactivation of non-enveloped virus by 1,5 iodonaphthylazide", BMC Res Notes, 8(44): 1-5 (dated Feb. 15, 2015).
Jackson, D.C. et al., "Antigenic determinants of influenza virus hemagglutinin II. Antigenic reactivity of the isolated N-Terminal cyanogen bromide peptide of A/memphis/72 hemagglutinin heavy chain", Virology, 93(2): 458-465 (Mar. 1979).
Raviv, Y. et al., "Hydrophobic Inactivation of Influenza Viruses Confers Preservation of Viral Structure with Enhanced Immunogenicity", J Virol, 82(9): 4612-4619 (Feb. 27, 2008).

* cited by examiner

*Primary Examiner* — Barry A Chestnut
(74) *Attorney, Agent, or Firm* — Proskauer Rose LLP; Fangli Chen

(57) ABSTRACT

The present invention provides, among other things, improved influenza vaccines based on hemagglutinins containing one or more alkylated cysteine residues. In particular, the present invention provides influenza vaccines containing hemagglutinins treated with an alkylating agent and methods of making the same. Inventive influenza vaccines provided by the present invention have a remarkable ability to retain potency as determined by Single Radial Immunodiffusion (SRID) assay upon storage.

13 Claims, 14 Drawing Sheets

ALKYLATED INFLUENZA VACCINES

CROSS REFERENCE TO RELATED APPLICATIONS

This application claims priority to U.S. Provisional Application 62/038,753 filed Aug. 18, 2014, which is incorporated by reference in its entirety.

BACKGROUND

Epidemic and pandemic influenza occurs annually and is a cause of significant morbidity and mortality worldwide. Influenza viruses are highly pleomorphic particles composed of two surface glycoproteins, hemagglutinin (HA) and neuraminidase (NA). The HA mediates attachment of the virus to the host cell and viral-cell membrane fusion during penetration of the virus into the cell. Therefore, an influenza vaccine typically contains an effective amount of HA that matches the diseases strain to induce production of neutralizing antibodies against the disease strain.

Single-radial-immunodiffusion (SRID) assays have been used to determine the Hemagglutinin (HA) content in the influenza vaccine and to measure potency of influenza virus vaccines licensed by the Food and Drug Administration for use in the United States since 1978. Specifically, SRID determines HA content in an influenza vaccine by using specific anti-HA antibodies. Samples of vaccines are applied onto an agar plate containing a strain-specific antiserum. The plates are typically incubated in a moist chamber at room temperature to allow diffusion of the antigen. Reaction of the antigen with the antibody produces a zone of precipitation (which is in form of precipitation ring). The amount of HA in the vaccine samples can be quantified by comparing the ring diameters of samples with the diameters of known concentrations of the reference HA protein. A potency value for the vaccine tested can be obtained based on the amount of HA.

SUMMARY

The present invention provides, among other things, improved influenza vaccines having a remarkable ability to retain potency as measured by SRID upon storage. The present invention is based in part on the surprising discovery that exposing HA antigens to alkylating agents (e.g., 2-Iodoacetamide (IOAM)) results in significantly reduced loss of HA potency as measured by SRID after storage. For example, as described in the Examples section, the present inventors have demonstrated that some IOAM treated HA antigens showed only approximately 1-5% loss in potency as measured by SRID assays after 6 months of storage. Without wishing to be bound by any particular theory, it is contemplated that a probable mechanism for the loss of HA potency over time is formation of intermolecular cysteine bonds. These covalent bonds prevent dissociation of HA rosette macrostructure upon zwittergent pretreatment and thereby restricting migration through the gel matrix, resulting in reduced interaction with the antisera. Treatment with alkylating agents results in alkylation of reactive cysteine groups of HA antigens, which prevents intermolecular disulfide bond formation. As a result, alkylated HA antigens provided by the present invention may better retain potency as measured by SRID after storage. Since SRID is one of the mostly commonly used measurements for determining the HA potency in an influenza vaccine and the only assay currently accepted by the FDA and other major health authorities, the present invention thus permits production of vaccines that ensure retention of required potency during the life of the vaccines.

In one aspect, the present invention provides an influenza vaccine comprising a hemagglutinin containing one or more alkylated cysteine residues. In some embodiments, the hemagglutinin contains 1-5, 1-4, 1-3, 2-5, 2-4, 2-3, 3-5, 3-4, or 4-5 alkylated cysteine residues. In some embodiments, the hemagglutinin contains 1, 2, 3, 4, or 5 alkylated cysteine residues. In some embodiments, the one or more alkylated cysteine residues constitute about 1-50%, 1-40%, 1-30%, 1-20% or 1-10% of total cysteine residues present in the hemagglutinin. In some embodiments, the one or more alkylated cysteine residues constitute about 10%, 20%, 30%, 40% or 50% of total cysteine residues present in the hemagglutinin. In some embodiments, substantially all free cysteine residues are alkylated. In some embodiments, the alkylated cysteine residues comprise methylated cysteine residues. In some embodiments, the hemagglutinin does not have non-specific alkylation and/or ubiquitous methylation. In some embodiments, the alkylated cysteine residues are determined by mass spectrometry.

In another aspect, the present invention provides an influenza vaccine comprising a hemagglutinin treated with an alkylating agent. As used herein, an alkylating agent suitable for the present invention may be any compound capable of alkylating cysteine sulfhydryl groups. In some embodiments, the alkylating agent is selected from the group consisting of 2-iodoacetamide (IOAM), iodoacetic acid, 2-bromoacetamide, glutathione bromoacetamide, bromoacetic acid, 1,3-propane sultone, methyl methanethiosulfonate, methoxycarbonylmethyl disulfide, maleamide, maleimide-PEG, vinylpyridine, N-ethylmaleimide, tosylacetamide, and combination thereof. In some embodiments, the alkylating agent is 2-iodoacetamide (IOAM).

In various embodiments, a hemagglutinin suitable for the present invention is an H1 protein present in a California or Solomon strain, a B protein present in a Brisbane, Fla., Ohio, Jiangsu or Hong Kong strain, and/or or a H3 protein present in a Victoria, Perth, Bristane or Wisconsin strain.

In some embodiments, an influenza vaccine provided by the present invention is a split influenza virus vaccine. In some embodiments, an influenza vaccine provided by the present invention is a recombinant influenza vaccine. In some embodiments, an influenza vaccine provided by the present invention is an egg based influenza vaccine. In some embodiments, an influenza vaccine provided by the present invention is produced in animal cells, plant cells, yeast cells, viral cells, fungus or algae, or synthetic cells. In some embodiments, suitable animal cells include, but are not limited to, insect cells, mammalian cells, and avian cells such as embryonated eggs, chicken embryo cells, and duck cell lines.

In some embodiments, an influenza vaccine provided by the present invention is a monovalent, divalent, trivalent or quadrivalent influenza vaccine.

In some embodiments, an influenza vaccine provided by the present invention retains at least about 90% (e.g., at least about 95%, 96%, 97%, 98%, 99%) potency as determined by Single Radial Immunodiffusion (SRID) assay upon storage of about 6 month at a temperature ranging from 1-30° C.

In some embodiments, an influenza vaccine provided by the present invention is substantially free of the alkylating agent.

In yet another aspect, the present invention provides a method of alkylating a hemagglutinin comprising a step of treating a purified hemagglutinin antigen or a hemagglutinin-containing viral particle with an alkylating agent. In some embodiments, a hemagglutinin-containing viral particle suitable for the present invention is a split virus. In some embodiments, a purified hemagglutinin antigen suitable for the present invention is a purified surface antigen. In some embodiments, a purified hemagglutinin antigen suitable for the present invention is a purified recombinant hemagglutinin protein. In some embodiments, a hemagglutinin suitable for the present invention is selected from an H1 protein present in a California or Solomon strain, a B protein present in a Brisbane, Fla., Ohio, Jiangsu or Hong Kong strain, or a H3 protein present in a Victoria, Perth, Bristane or Wisconsin strain.

In still another aspect, the present invention provides a method of manufacturing an influenza vaccine comprising a step of treating a viral particle obtained from an influenza virus produced from an egg based or cell culture based production system with an alkylating agent. In some embodiments, a viral particle suitable for the present invention is obtained by splitting the influenza virus.

In a further aspect, the present invention provides a method of manufacturing an influenza vaccine, comprising: harvesting influenza virus from an egg based or cell culture based production system; splitting the influenza virus; treating the split influenza virus with an alkylating agent; and inactivating the treated split influenza virus.

In various embodiments, the splitting step comprises treating the influenza virus with a detergent. In some embodiments, a suitable detergent is selected from Triton® (a nonionic surfactant that has a hydrophilic polyethylene chain), sodium taurodeoxycholate, nonylphenol ethoxylate, cetyltrimethylammonium bromide (CTAB), and/or sodium deoxycholate. In some embodiments, the detergent is Triton® (e.g., Triton® X-100, Triton® N-101, Triton® 720 and/or Triton® X-200).

In some embodiments, a suitable alkylating agent is selected from the group consisting of 2-iodoacetamide (IOAM), iodoacetic acid, 2-bromoacetamide, glutathione bromoacetamide, bromoacetic acid, 1,3-propane sultone, methyl methanethiosulfonate, methoxycarbonylmethyl disulfide, maleamide, maleimide-PEG, vinylpyridine, N-ethylmaleimide, tosylacetamide, and combination thereof. In some embodiments, a suitable alkylating agent is 2-iodoacetamide (IOAM).

In some embodiments, an influenza virus suitable for the present invention is produced in the egg based production system. In some embodiments, a suitable influenza virus is produced in animal cells, plant cells, yeast cells, viral cells, fungus or algae. In some embodiments, suitable animal cells include, but are not limited to, insect cells, mammalian cells, and avian cells such as embryonated eggs, chicken embryo cells, and duck cell lines.

In some embodiments, the step of treating comprises incubating the purified hemagglutinin antigen, the hemagglutinin-containing viral particle, the viral particle, or the split influenza virus described herein with the alkylating agent at a temperature ranging between 1-30° C. In some embodiments, a suitable temperature is room temperature. In some embodiments, a suitable temperature ranges between 1-5° C., 2-8° C., 5-10° C., 10-15° C., 15-20° C., 20-25° C., or 25-30° C.

In some embodiments, the step of treating comprises incubating the purified hemagglutinin antigen, the hemagglutinin-containing viral particle, the viral particle, or the split influenza virus described herein with the alkylating agent for up to about 24 hours, 20 hours, 18 hours, 16 hours, 14 hours, 12 hours, 10 hours, 8 hours, 6 hours, 4 hours, 2 hours, 1.5 hours, 1 hour, 50 minutes, 40 minutes, 30 minutes, 20 minutes, or 10 minutes.

In some embodiments, the alkylating agent is present at a concentration of more than about 1× molar excess to hemagglutinin (HA)-cysteine concentration. In some embodiments, the alkylating agent is present at a concentration ranging from about 1X to 100X, from 5X to 85X, from 1X to 50X, or from 5X to 50X molar excess to hemagglutinin (HA)-cysteine concentration.

In some embodiments, the alkylating agent is present at a concentration ranging from about 1 mM-1 M, 1 mM-500 mM, 1 mM-400 mM, 1 mM-300 mM, 1 mM-200 mM, or 1 mM-100 mM. In some embodiments, the alkylating agent is present at a concentration of about 1 mM, 10 mM, 20 mM, 30 mM, 40 mM, 50 mM, 100 mM, 200 mM, 300 mM, 400 mM, or 500 mM. In some embodiments, the alkylating agent is present at a concentration ranging from about 1 µg/ml-1, 000 µg/ml, 1 µg/ml-500 µg/ml, 1 µg/ml-400 µg/ml, 1 µg/ml-300 µg/ml, 1 µg/ml-200 µg/ml, or 1 µg/ml-100 µg/ml. In some embodiments, the alkylating agent is present at a concentration of about 1 µg/ml, 10 µg/ml, 20 µg/ml, 30 µg/ml, 40 µg/ml, 50 µg/ml, 60 µg/ml, 70 µg/ml, 80 µg/ml, 90 µg/ml, 100 µg/ml, 200 µg/ml, 300 µg/ml, 400 µg/ml, or 500 µg/ml.

In some embodiments, the step of treating with the alkylating agent results in alkylation of one of more cysteine residues of hemagglutinin. In some embodiments, the step of treating with the alkylating agent results in alkylation of 1-5, 1-4, 1-3, 2-5, 2-4, 2-3, 3-5, 3-4, or 4-5 cysteine residues. In some embodiments, the step of treating with the alkylating agent results in alkylation of 1, 2, 3, 4, or 5 cysteine residues. In some embodiments, the step of treating with the alkylating agent results in alkylation of about 1-50%, 1-40%, 1-30%, or 1-20% total cysteine residues present in the hemagglutinin. In some embodiments, the step of treating with the alkylating agent results in alkylation of about 10%, 20%, 30%, 40% or 50% total cysteine residues present the hemagglutinin. In some embodiments, the step of treating with the alkylating agent results in alkylation of substantially all free cysteine residues present in the hemagglutinin. In some embodiments, treatment with the alkylating agent does not result in non-specific alkylation. In some embodiments, treatment with the alkylating agent does not result in ubiquitous methylation.

In various embodiments, treatment with the alkylating agent results in reduced potency loss of the influenza vaccine determined by Single Radial Immunodiffusion (SRID) as compared to an otherwise identical influenza vaccine without the treatment of the alkylating agent.

In some embodiments, treatment with the alkylating agent results in no more than about 50% (e.g., no more than about 40%, 30%, 20%, 10%, 5%, 4%, 3%, 2%, or 1%) potency loss determined by SRID when the influenza vaccine is stored at 1-30° C. for 30 days.

In some embodiments, the step of treating with the alkylating agent is performed prior to a step of inactivating the influenza virus. In other embodiments, the step of treating with the alkylating agent is performed concurrently with a step of inactivating the influenza virus.

In some embodiments, the inactivating step comprises treating the influenza virus with ultraviolet light or a chemical inactivating agent. In some embodiments, the inactivating step comprises treating the influenza virus with a chemical inactivating agent selected from beta-propiolactone, sodium deoxycholate, and/or formalin. In particular embodiments, the inactivating step comprises treating the influenza virus with formalin.

In some embodiments, a method according to the present invention further includes a step of removing the alkylating agent. In some embodiments, the alkylating agent is removed by diafiltration. In some embodiments, the alkylating agent is removed together with the chemical inactivating agent.

Among other things, the present invention provides an influenza vaccine manufactured according to a method described herein. In various embodiments, an influenza vaccine provided by the present invention is a monovalent, divalent, trivalent or quadrivalent influenza vaccine. In various embodiments, an influenza vaccine of the present invention can be provided as a single-dose, multi-dose, adult-dose or pediatric-dose vaccine. In some embodiments, each individual dose may be presented in a vial, a syringe including a pediatric syringe, or other type of container. In various embodiments, an influenza vaccine of the present invention may be formulated for intradermal, intramuscular, subcutaneous, intravenous, and other mode of administration. Additional dosing, formulations, administration routes are described throughout the specification, for example, in the "Immunogenic Vaccine Compositions" section.

As used herein, "potency" or "stability" as determined by a Single Radial Immunodiffusion (SRID) assay encompasses "apparent potency" or "apparent stability", respectively.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE FIGURES

The drawings are for illustration purposes only, not for limitation.

FIG. 5 depicts an exemplary structural mechanism underlying reduced HA potency loss resulting from treatment of HA with an alkylating agent.

FIG. 8 depicts exemplary data illustrating the impact of IOAM concentration on stabilizing HA potency.

DEFINITIONS

Figure 1:
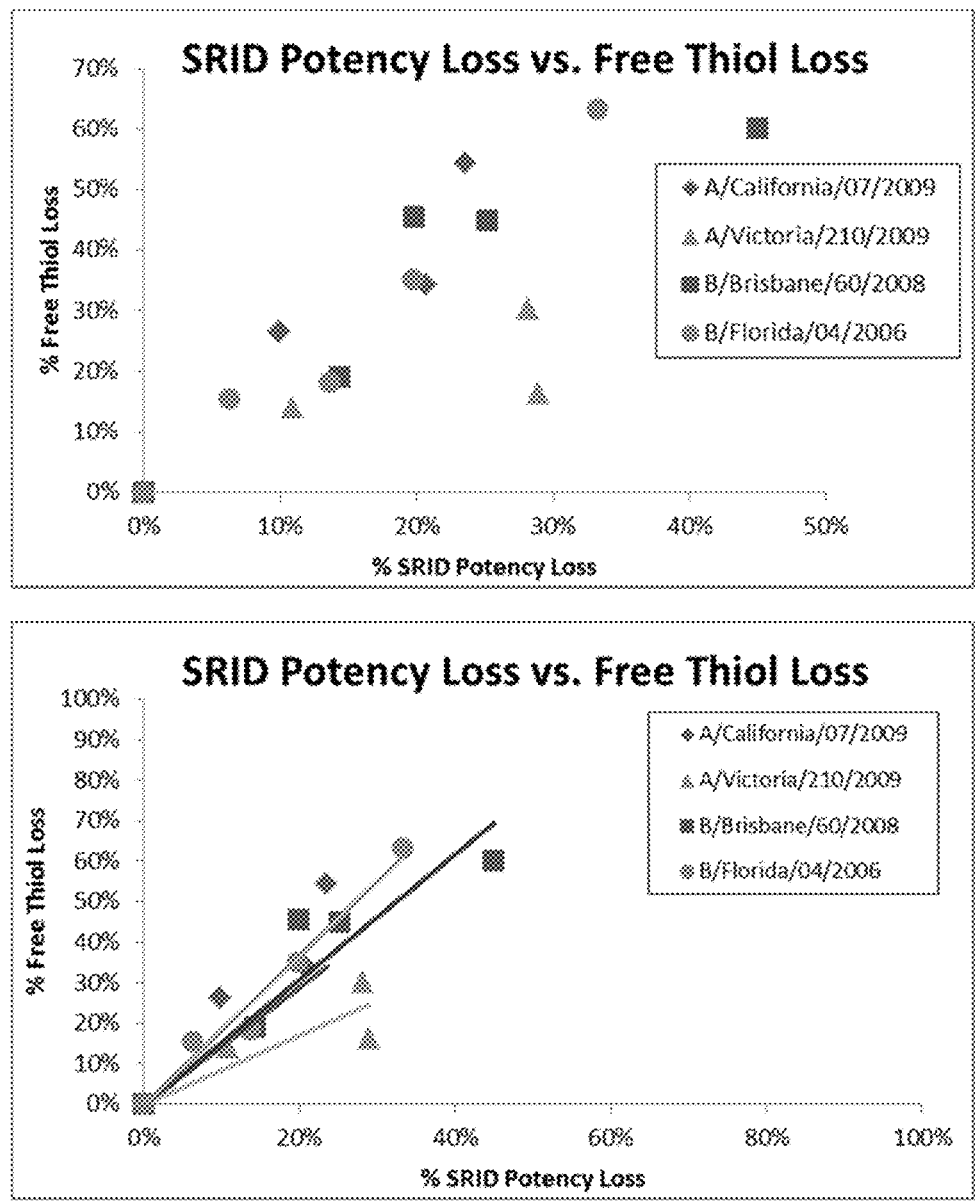
FIG. 1 depicts exemplary data illustrating the correlation of percent potency loss by SRID and free thiols in HA based on data from different strains.

In order for the present invention to be more readily understood, certain terms are first defined below. Additional definitions for the following terms and other terms are set forth throughout the specification.

Adjuvant: As used herein, the term "adjuvant" refers to a substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administer: As used herein, "administering" a composition to a subject means to give, apply or bring the composition into contact with the subject. Administration can be accomplished by any of a number of routes, such as, for example, topical, oral, subcutaneous, intramuscular, intraperitoneal, intravenous, intrathecal and intradermal.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Alkylating Agent: As used herein, the term "alkylating agent" refers to any chemical or non-chemical substance capable of carrying out the transfer of an alkyl group from one molecule to another. Alkyl groups can include: an alkyl carbocation, a carbanion, a free radical, a carbine, and a methyl group. In its simplest form, alkylation can encompass methylation—the transfer of only one carbon group. In some embodiments, the term "alkylating agents" includes methylating agents.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Antibody: As used herein, the term "antibody" refers to an immunoglobulin molecule produced by B lymphoid cells with a specific amino acid sequence. In some embodiments, antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies. In some embodiments, the term "antibodies" refers to any recombinant antibodies used in in vitro assays, such as in SRID assays, including one or more polypeptides substantially encoded by immunoglobulin genes or fragments of immunoglobulin genes. Such antibodies may exist as intact immunoglobulins or as fragments of the immunoglobulin classes, IgG, IgM, IgA, IgD and IgE, respectively. Exemplary antibody fragments include, but are not limited to, F(ab)'2, Fab', and single chain Fv (scFv).

Antigen: As used herein, the term "antigen" refers to a compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In some embodiments of the disclosed compositions and methods, an influenza HA protein is an antigen.

Engineered: As used herein, the term "engineered" refers to a polypeptide whose amino acid sequence has been modified by man. For example, an engineered HA polypeptide has an amino acid sequence that differs from the amino acid sequences of HA polypeptides found in natural influenza isolates. In some embodiments, an engineered HA polypeptide has an amino acid sequence that differs from the amino acid sequence of HA polypeptides included in the NCBI database.

H1 polypeptide: An "H1 polypeptide", as that term is used herein, is an HA polypeptide whose amino acid sequence includes at least one sequence element that is characteristic of H1 and distinguishes H1 from other HA subtypes.

H3 polypeptide: An "H3 polypeptide", as that term is used herein, is an HA polypeptide whose amino acid sequence includes at least one sequence element that is characteristic of H3 and distinguishes H3 from other HA subtypes.

H5 polypeptide: An "H5 polypeptide", as that term is used herein, is an HA polypeptide whose amino acid sequence includes at least one sequence element that is characteristic of H5 and distinguishes H5 from other HA subtypes.

Hemagglutinin (HA): As used herein, the term "hemagglutinin," "hemagglutinin polypeptide," or "hemagglutinin protein" refers to any naturally occurring or recombinant, including engineered, hemagglutinin. A wide variety of HA sequences from influenza isolates are known in the art; indeed, the National Center for Biotechnology Information (NCBI) maintains a database (http://www.ncbi.nlm.nih.gov/genomes/FLU/) that, as of the filing of the present application included at least 9796 HA sequences. Those of ordinary skill in the art, referring to this database, can readily identify sequences that are characteristic of HA polypeptides generally, and/or of particular HA polypeptides (e.g., H1, H2, H3, H4, H5, H6, H7, H8, H9, H10, H11, H12, H13, H14, H15, or H16 polypeptides; or of HAs that mediate infection of particular hosts, e.g., avian, camel, canine, cat, civet, environment, equine, human, leopard, mink, mouse, seal, stone martin, swine, tiger, whale, etc.).

Immune response: As used herein, the term "immune response" refers to a response of a cell of the immune system, such as a B cell, T cell, macrophage or polymorphonucleocyte, to a stimulus such as an antigen or vaccine. An immune response can include any cell of the body involved in a host defense response, including for example, an epithelial cell that secretes an interferon or a cytokine An immune response includes, but is not limited to, an innate immune response or inflammation. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

Immunogen: As used herein, the term "immunogen" refers to a compound, composition, or substance which is capable, under appropriate conditions, of stimulating an immune response, such as the production of antibodies or a T cell response in an animal, including compositions that are injected or absorbed into an animal. As used herein, an "immunogenic composition" is a composition comprising an immunogen (such as an HA polypeptide). As used herein, "immunize" means to render a subject protected from an infectious disease, such as by vaccination.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Influenza virus: As used herein, the term "influenza virus" refers to a segmented negative-strand RNA virus that belongs to the Orthomyxoviridae family. There are three types of Influenza viruses, A, B, and C. Influenza A viruses infect a wide variety of birds and mammals, including humans, horses, marine mammals, pigs, ferrets, and chickens. In animals, most influenza A viruses cause mild localized infections of the respiratory and intestinal tract. However, highly pathogenic influenza A strains, such as H5N1, cause systemic infections in poultry in which mortality may reach 100%. In 2009, H1N1 influenza was the most common cause of human influenza. A new strain of swine origin H1N1 emerged in 2009 and was declared pandemic by the World Health Organization. This strain was referred to as "swine flu." H1N1 influenza A viruses were also responsible for the Spanish flu pandemic in 1918, the Fort Dix outbreak in 1976, and the Russian flu epidemic in 1977-1978.

Influenza vaccine: As used herein, the term "influenza vaccine" refers to a preparation of immunogenic material capable of stimulating an immune response, administered for the prevention, amelioration, or treatment of disease, such as influenza virus infection. The immunogenic material may include, for example, attenuated or killed microorganisms (such as attenuated viruses), or antigenic proteins, peptides or DNA derived from them, or any recombinant versions of such immunogenic materials.

Isolated: The term "isolated", as used herein, refers to an agent or entity that has either (i) been separated from at least some of the components with which it was associated when initially produced (whether in nature or in an experimental setting); or (ii) produced by the hand of man. Isolated agents or entities may be separated from at least about 10%, at least about 20%, at least about 30%, at least about 40%, at least about 50%, at least about 60%, at least about 70%, at least about 80%, at least about 90%, or more of the other components with which they were initially associated. In some embodiments, isolated agents are more than 90%, 91%, 92%, 93%, 94%, 95%, 96%, 97%, 98%, 99% pure.

Outbreak: As used herein, an influenza virus "outbreak" refers to a collection of virus isolates from within a single country in a given year.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic compositions, such as one or more influenza vaccines, and additional pharmaceutical agents. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Recombinant: As used herein, the term "recombinant" refers to a recombinant nucleic acid or protein which is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques.

Recombinant influenza vaccine: As used herein, the term "recombinant influenza vaccine" refers to influenza vaccines produced using reverse genetics methods, including, but not limited to, virus-like particles, and DNA- and viral vector-based vaccines.

SRID assay: As used herein, the term "SRID" (Single Radial Immunodiffusion) assay refers to protocols for quantitating the amount of HA antigen in a sample. In general, a SRID assay measures the amount of antigen/antibody that precipitates around a well into which detergent solubilized virus is placed and allows the determination of HA concentration relative to an official reference antigen, such as, A/California/07/2009. Specifically, an agarose solution containing a pre-determined amount of polyclonal antibody is plated in a thin gel layer punched with 3-4 mm holes. Dilutions of standard HA reference antigen are placed into the wells alongside samples with unknown HA concentrations. The gel is incubated and resulting precipitin rings are visualized following Coomassie blue stain of the gel. Ring diameters are measured and compared to a standard curve in order to calculate influenza vaccine HA potency.

Subject: As used herein, the term "subject" refers to a living multi-cellular vertebrate organisms, a category that includes both human and non-human mammals, such as non-human primates.

Substantially: As used herein, the term "substantially" refers to an amount greater than 80%, 85%, 90%, 95%, 96%, 97%, 98%, 99% of the total amount.

Vaccination: As used herein, the term "vaccination" refers to the administration of a composition intended to generate an immune response, for example to a disease-causing agent. For the purposes of the present invention, vaccination can be administered before, during, and/or after exposure to a disease-causing agent, and in some embodiments, before, during, and/or shortly after exposure to the agent. In some embodiments, vaccination includes multiple administrations, appropriately spaced in time, of a vaccinating composition.

Wild type: As is understood in the art, the phrase "wild type" generally refers to a normal form of a protein or nucleic acid, as is found in nature. For example, wild type HA polypeptides are found in natural isolates of influenza virus. A variety of different wild type HA sequences can be found in the NCBI influenza virus sequence database, available through the world wide web at ncbi.nlm.nih.gov/genomes/FLU/FLU.

DETAILED DESCRIPTION

The present invention provides, among other things, improved influenza vaccines based on hemagglutinins containing one or more alkylated cysteine residues. In particular, the present invention provides influenza vaccines containing hemagglutinins treated with an alkylating agent and methods of making the same. Inventive influenza vaccines provided by the present invention have a remarkable ability to retain potency as determined by Single Radial Immunodiffusion (SRID) assay upon storage.

Various aspects of the invention are described in further detail in the following subsections. The use of subsections is not meant to limit the invention. Each subsection may apply to any aspect of the invention. In this application, the use of "or" means "and/or" unless stated otherwise.

Influenza Vaccines

The present invention is applicable to any influenza vaccines. In general, the influenza viruses are divided into types A, B and C based on antigenic differences. Influenza A viruses are described by a nomenclature which includes the sub-type or type, geographic origin, strain number, and year of isolation, for example, A/Beijing/353/89. There are at least 18 sub-types of HA (H1-H18) and 11 subtypes of NA (N1-N11). Some subtypes such as H1-H3 and N1-N2 are commonly found in humans (Murphy and Webster, "Orthomyxoviruses", in Virology, ed. Fields, B. N., Knipe, D. M., Chanock, R. M., 1091-1152 (Raven Press, New York, (1990)).

Antibodies to HA neutralize the virus and form the basis for natural immunity to infection by influenza (Clements, "Influenza Vaccines", in Vaccines: New Approaches to Immunological Problems, ed. Ronald W. Ellis, pp. 129-150 (Butterworth-Heinemann, Stoneham, Mass. 1992)). Influenza vaccines typically contain an effective amount of suitable HA to elicit neutralizing antibodies.

The presence of influenza HA-specific neutralizing IgG and IgA antibody is associated with resistance to infection and illness (Clements, 1992). Inactivated whole virus or partially purified (split subunit) influenza vaccines are standardized to the quantity of HA from each strain. Many licensed influenza vaccines include formalin-inactivated whole or chemically split subunit preparations from two influenza A subtype (H1N1 and H3N2) and one influenza B subtype viruses.

In some embodiments, seed viruses for influenza A and B vaccines are naturally occurring strains that accumulate to high titers in the allantoic fluid of chicken eggs. Alternatively, the strain for the influenza A component is a reassortant virus with the correct surface antigen genes. A reassortant virus is one that, due to segmentation of the viral genome, has characteristics of each parental strain. When more than one influenza viral strains infect a cell, these viral segments mix to create progeny virion containing various assortments of genes from both parents.

The present invention may be applied to various vaccines of any influenza strain of type A, B or C. In particular, the present invention may be applied to various vaccines of any influenza strain of type A, B or C capable of infecting humans, including those existed in the past, present and those that will occur in the future. In some embodiments, the present invention may be applied to various influenza vaccines, including vaccines of different strains including, but not limited to, H1, H2, H3, H4, H5, H6, H7, H8, H9, H10, H11, H12, H13, H14, H15, H16, H17, and H18. In some embodiments, embodiments of the present invention can be applied to various influenza vaccines of pandemic or endemic strains, including but not limited to H1N1, H2N2, H3N2, H3N8, H5N1, H7N7, H7N9, H1N2, H9N2, H7N2, H10N7, H17N10, and H18N11.

As non-limiting examples, the present invention may be applied to influenza strains including, but not limited to, turkey influenza virus strain A/Turkey/Ireland/1378/83 (H5N8), turkey influenza virus strain A/Turkey/England/63 (H7N3), turkey influenza virus strain A/Turkey/England/66 (H6N2), A/Turkey/England/69 (H7N2), A/Turkey/Scotland/70 (H6N2), turkey influenza virus strain A/Turkey/England N28/73 (H5N2), turkey influenza virus strain A/Turkey/England/110/77 (H6N2), turkey influenza virus strain A/Turkey/England/647/77 (H1N1), turkey influenza virus strain A/Turkey/Ontario/7732/66 (H5N9), turkey influenza virus strain A/Turkey/England/199/79 (H7N7), turkey influenza virus strain A/Turkey/Ontario/7732/66 (H5N9), turkey influenza virus strain A/Turkey/Ireland/1378/85 (H5N8), turkey influenza virus strain A/Turkey/England/50-92/91 (H5N1), turkey influenza virus strain A/Turkey/Wisconsin/68 (H5N9), turkey influenza virus strain A/Turkey/Massachusetts/65 (H6N2), turkey influenza virus strain A/Turkey/Oregon/71 (H7N3), turkey influenza virus strain A/Turkey/Ontario/6228/67 (H8N4), turkey influenza virus strain A/Turkey/Wisconsin/66 (H9N2), turkey influenza virus strain A/Turkey/England/647/77 (H1N1), turkey influenza virus strain A/Turkey/Ontario/6118/68 (H8N4), turkey influenza virus strain A/Tur/Ger 3/91, turkey influenza virus strain A/Turkey/Minnesota/833/80 (H4N2) chicken influenza virus strain A/Chicken/Indonesia/03 (H5N1), chicken influenza virus strain A/Chicken/FPV/Rostock/1934, chicken influenza virus strain A/Chicken/Texas/298313/04, chicken influenza virus strain A/Chicken/Texas/167280-4-/02, chicken influenza virus strain A/Chicken/Hong Kong/220/97, chicken influenza virus strain A/Chicken/Italy/8/98, chicken influenza virus strain A/Chicken/Victoria/7 6 (H7N7), chicken influenza virus strain A/Chicken/Germany/79 (H7N7), chicken influenza virus strain A/Chicken/Scotland/59 (H5N1), chicken influenza virus strain A/Chicken/Pennsylvania/1370/83 (H5N2), chicken influenza virus strain A/Chicken/Queretaro-19/95 (H5N2), chicken influenza virus strain A/Chicken/Queretaro-20/95 (H5N2), chicken influenza virus strain A/Chicken/Hong Kong/258/97 (H5N1), chicken influenza virus strain A/Chicken/Italy/1487/97 (H5N2), chicken influenza virus strain A/Chicken/Leipzig/79 (H7N7), chicken influenza virus strain A/Chicken/Victoria/185 (H7N7), chicken influenza virus strain A/Chicken/Victoria/92 (H7N3), chicken influenza virus strain A/Chicken/Queensland/95 (H7N3), chicken influenza virus strain A/Chicken/Pakistan/1369/95 (H7N2), chicken influenza virus strain A/Chicken/Pakistani 447-4/95 (H7N3), chicken influenza virus strain A/Chicken/HK/G9/97 (H9N2), chicken influenza virus strain A/Chicken/Nakom-Patom/Thailand/CU-K2/2004 (H5N1), chicken influenza virus strain A/Chicken/Hong Kong/31.2/2002 (H5N11), chicken influenza virus strain A/Chicken/Vietnam/C58/04 (H5N1), chicken influenza virus strain A/Chicken/Vietnam/38/2004 (H5N1), chicken influenza virus strain A/Chicken/Alabama/7395/75 (H4N8), chicken influenza virus strain A/Chicken/Germany/N/49 (H10N7), chicken influenza virus strain A/Chicken/Beijing/1/94 (H9N2), chicken influenza virus strain A/Chicken/Hong Kong/G23/97 (H9N2), chicken influenza virus strain A/Chicken/Pennsylvania/8125/83 (H5N2), chicken influenza virus strain A/Chicken/Hong Kong/97 (H5N1), duck influenza virus strain A/Duck/Anyang/AVL-1/01, duck influenza virus strain A/Duck/New York/17542-4/86 (H9N1), duck influenza virus strain A/Duck/Alberta/28/76 (H4N6), duck influenza virus strain A/Duck/Nanchang/4-165/2000 (H4N6), duck influenza virus strain A/Duck/Germany/49 (H10N7), duck influenza virus strain A/Black Duck/Australia/702/78 (H3N8), duck influenza virus strain A/Duck/Vietnam/11/2004 (H5N1), duck influenza virus strain A/Duck/Alberta/60/76 (H12N5), duck influenza virus strain A/Duck/Hong Kong/196/77 (H1), duck influenza virus strain A/Duck/Wisconsin/1938/80 (H1N1), duck influenza virus strain A/Duck/Bavaria/2/77 (H1N1N1), duck influenza virus strainA/Duck/Bavaria/1/77 (H1N1), duck influenza virus strain A/Duck/Australia/749/80 (H1N1), duck influenza virus strain A/Duck/Hong Kong/Y280/97 (H9N2), duck influenza virus strain A/Duck/Alberta/35/76H1N1) (see, e.g., Austin etal., 1990), avian influenza virus strain A/Mallard duck/Gurjev/263/82 (H14N5), avian influenza virus strain A/Mallard duck/PA/10218/84 (H5N2), avian influenza virus strain A/Mallard duck/Astrakhan/244/82 (H14N6), goose influenza virus strain A/Goose/Guangdong/1/96, goose influenza virus strainA/Goose/Leipzig/137-8/79 (H7N7), goose influenza virus strain A/Goose/Hong Kong/W222/97 (H6N7), goose influenza virus strain A/Goose/Leipzig/187-7/79 (H7N7), goose influenza virus strain A/Goose/Leipzig/192-7/79 (H7N7), avian influenza virus strain A/Env/HK/437-4/99, avian influenza virus strain A/Env/HK/437-6/99, avian influenza virus strain A/Env/HK/43 7-8/99, avian influenza virus strain A/Env/HK/437-10/99, avian influenza virus strain A/Fowl plague virus strain/Dutch/27 (H7N7), avian influenza virus strain A/Fowl plague virus strain/Dobson/27 (H7N7) (see, e.g., Horimoto eta!., 2001), avian influenza virus strain A/Fowl plague virus strain/Rostock/34 (H7N1), avian influenza virus strain A/Fowl plague virus strain/Egypt/45 (H7N1), avian influenza virus strain A/Fowl plague virus strain/Weybridge (H7N7), avian influenza virus strain A/Tern/South Africa/61 (H5N3), avian influenza virus strain A/Tern/Australia/G70C/75 (H11N9), avian influenza virus strain A/QuailNietnam/36/04 (H5N1), avian influenza virus strain A/Gull/Maryland/704/77 (H13N6), avian influenza virus strain A/Black-headed gull/Sweden/5/99 (H16N3), avian influenza virus strain A/Herring gull/DE/677/88 (H2N8), avian influenza virus strain A/Swan/Italy/179/06 (H5N1), avian influenza virus strain A/Hong Kong/156/97 (A/HK/156/97), avian influenza virus strain A/Quail/HK/G1/97 (H9N2), avian influenza virus strain A/Quail/Hong Kong/AF157/93 (H9N2), avian influenza virus strain A/Teal/HK/W312/97 (H6N1), avian influenza virus strain A/Shearwater/West Australia/2576/79 (H15N9), avian influenza virus strain A/Shearwater/Australia/72 (H6N5), avian influenza virus strain A/Hong Kong/212/03, avian influenza virus strain A/England/321/77 (H3N2), avian pandemic influenza A viruses of avian origin avian H5N1 influenza virus, avian H7N1 influenza strain, avian H9N2 influenza virus, and avian influenza virus, cold-adapted (ca) and temperature sensitive (ts) master donor strain, A/Leningrad/134/17/57 (H2N2), the disclosures of which are incorporated by reference. Other influenza strains that may be used in methods of the present invention include, but are not limited to, equine influenza virus (A/Equi 2 (H3N8), Newmarket 1/93), equine-2 influenza virus (EIV; subtype H3N8), equine-2 influenza virus, A/Equine/Kentucky/1/91 (H3N8), equine influenza virus strain A/Equine/Berlin/2/91 (H3N8), equine influenza virus strain A/Equine/Cambridge/1/63 (H7N7), equine influenza virus strain A/Equine/Prague/1/56 (H7N7), equine influenza virus strain A/Eq/Kentucky/98, equine influenza virus strain A/Equi 2 (Kentucky 81), equine influenza virus strain A/Equine/Kentucky/1/81 (Eq/Ky) equine influenza virus strain A/Equine Kentucky/1/81 (H3N8), equine influenza virus strain A/Equine/Kentucky/1/91 (H3N8), equine influenza virus strain A/Equine/Kentucky/1277/90 (Eq/Kentucky), equine influenza virus strain A/Equine/Kentucky/2/91 (H3N8), equine influenza virus strain A/Equine/Kentucky/79 (H3N8), equine influenza virus strain A/Equine/Kentucky/81, equine influenza virus strain A/Equine/Kentucky/91 (H3N8), equine influenza virus strain A/Equine-2/Kentucky/95 (H3N8) and equine influenza virus strain A/Equine-2/Kentucky/98, equine influenza virus strainA/Eq/Newmarket/1/77, equine influenza virus strain A/Eq/Newmarket/5/03, equine influenza virus strain A/Equi 2 (H3N8), Newmarket 1/93, equine influenza virus strain A/Equi-2/Newmarket-1/93, equine influenza virus strain A/Equine/Newmarket/2/93, equine influenza virus strain A/Equine/Newmarket/79 (H3N8), equine influenza virus strain A/Equine/Newmarket/1/77 (H7N7) and equine influenza virus strain A/Equine-2/Newmarket-2/93, equine influenza virus strain A/Eq/Miami/63 (H3N8), A/Equi1 (Prague strain), equine influenza virus strain A/Equi 2 (Miami), equine influenza virus strainA/Equi-1/Prague/56 (Pr/56), equine influenza virus strainA/Equi-2/Suffolk/89 (Suf/89), equine influenza virus strain A/Equine 2/Sussex/89 (H3N8), equine influenza virus strain A/Equine/Sussex/89, equine influenza virus strain A/Equine-2/Saskatoon/90, equine influenza virus strain A/Equine/Prague/1/56 (H7N7), equine influenza virus strain A/Equine/Miami/1/63 (H3N8), A/Aichi/2/68 (H3N2), equine influenza virus strain A/Equine/Tokyo/2/71 (H3N8), equine influenza virus strain A/Eq/LaPlata/1/88, equine influenza virus strain A/Equine/Jilin/1/89 (Eq/Jilin), equine influenza virus strain A/Equine/Alaska/1/91 (H3N8), equine influenza virus strain A/Equine/Saskatoon/1/91 (H3N8), equine influenza virus strain A/Equine/Rome/5/91 (H3N8), equine influenza virus strain A/Equine/La Plata/1/93 (H3N8), equine influenza virus strain A/Equine/La Plata/1/93 (LP/93), equine influenza virus strain A/Eq/Holland/1/95 (H3N8) and equine influenza virus strain A/Eq/Holland/2/95 (H3N8), human influenza virus A(H3N2) isolates, human influenza virus A/Memphis/1/71 (H3N2), human influenza virus A/Nanchang/933/95 (H3N2) virus, human influenza virus A/PR/8/34 (H1N1) virus, human influenza virus A/Singapore/57 (H2N2) virus, influenza virus A, influenza virus A/HK/213/03, influenza virus strain A/HK/483/97, influenza virus strain A/Thailand/S(KK-494)/2004 (H5N1), influenza virus strain A PR/8/34 (PR8) virus strain (H1N1subtype), influenza virus strain A/Aichi/2/68 (H3N2), influenza virus strain AI Ann Arbor/6/60 cold-adapted virus strain, influenza virus strain A/Beijing 32/92 (H3N2), influenza virus strain A/Charlottesville/31/95 (H1N1), influenza virus strain A/Kawasaki/86 (H1N1) virus strain, influenza virus strain A/Korea/82 (H3N2), influenza virus strain A/Leningrad/134/57, influenza virus strain A/NWS/33 (H1N1), influenza virus strain A/PR/8/34 (H1N1), influenza virus strain A/PR8/34, influenza virus strain A/Puerto Rico (PR)/8/34, influenza virus strain A/Puerto Rico/8-Mount Sinai, influenza virus strain A/Shangdong 9/93 (H3N2), influenza virus strain A/Shingapore/1/57 (H2N2), influenza virus strain A/Singapore 6/86 (H1N1), influenza virus strain A/Singapore/1/57 (H2N2), influenza virus strain A/Texas 36/91 (H1N1), influenza virus strainA/Texas/36/91 (H1N1) virus strain, influenza virus strain A/Texas/36/91 (H1N1), influenza virus strain A/Udorn/72 virus infection, influenza virus A/Victoria/3/75 (H3N2), influenza virus A/Virginia/88 (H3N2), influenza virusA/WSN/33 (H1N1), influenza virus A/WSN/33, influenza virus B, influenza virus B/Ann Arbor 1/86, influenza virus B/Harbin/7/94, influenza virus B/Hong Kong/5/72, influenza virus B/Lee/40, influenza virus BNamagata 16/88, influenza virus B/Yamagata group, influenza virus BNamanashi/166/98, influenza virus C, influenza virus strain A/Equi/2/Kildare/89, influenza virus type B/Panama 45/90, live, cold-adapted, temperature-sensitive (ca/ts) Russian influenza A vaccines, swine H1 and H3 influenza viruses, swine influenza A viruses, swine influenza virus (SIV), swine influenza virus A/Sw/Ger 2/81, swine influenza virus A/Sw/Ger 8533/91, swine influenza virus strain A/Swine/Wisconsin/125/97 (H1N1), swine influenza virus strain A/Swine/Wisconsin/136/97 (H1N1), swine influenza virus strain A/Swine/Wisconsin/63/97 (H1N1), swine influenza virus strain A/Swine/Wisconsin/164/97 (H1N1), swine influenza virus strain A/Swine/Wisconsin/166/97 (H1N1), swine influenza virus strain A/Swine/Wisconsin/168/97 (H1N1), swine influenza virus strain A/Swine/Wisconsin/235/97 (H1N1), swine influenza virus strain A/Swine/Wisconsin/238/97 (H1N1), swine influenza virus strain A/Swine/Wisconsin/457/98 (H1N1), swine influenza virus strain A/Swine/Wisconsin/458/98 (H1N1), swine influenza virus strain A/Swine/Wisconsin/464/98 (H1N1), swine influenza virus strain A/Swine/Indiana/1726/88 (H1N1), swine influenza virus strain A/Swine/Indiana/9K035/99 (H1N2), swine influenza virus strain A/Swine/Nebraska/1/92 (H1N1), swine influenza virus strain A/Swine/Quebec/91 (H1N1), swine influenza virus strain A/Swine/Quebec/81 (H1N1), swine influenza virus strain A/Swine/New Jersey/11/76 (H1N1), swine influenza virus strain A/Swine/Ehime/1/80 (H1N2), swine influenza virus strain A/Swine/England/283902/93 (H1N1), swine influenza virus strain A/Swine/England/195852/92 (H1N1), swine influenza virus strain A/Swine/Germany/8533/91 (H1N1), swine influenza virus strain A/Swine/Germany/2/81 (H1N1), swine influenza virus strain A/Swine/Nebraska/209/98 (H3N2), A/Swine/Iowa/533/99 (H3N2), swine influenza virus strain A/Swine/Iowa/569/99 (H3N2), swine influenza virus strain A/Swine/Minnesota/593/99 (H3N2), swine influenza virus strain A/Swine/Iowa/8548-1/98 (H3N2), swine influenza virus strain A/Swine/Minnesota/9088-2/98 (H3N2), swine influenza virus strain A/Swine/Texas/4199-2/98 (H3N2), swine influenza virus strain A/Swine/Ontario/41848/97 (H3N2), swine influenza virus strain A/Swine/North Carolina/35922/98 (H3N2), A/Swine/Colorado/1/77 (H3N2), swine influenza virus strain A/Swine/Hong Kong/3/76 (H3N2), swine influenza virus strain A/Swine/Hong Kong/13/77 (H3N2), swine influenza virus strain A/Swine/Nagasaki/1/90 (H1N2), swine influenza virus strain A/Swine/Nagasaki/1/89 (H1N2), swine influenza virus strain A/Swine/Wisconsin/1915/88 (H1N1), swine influenza virus strain A/Swine/Iowa/17672/88 (H1N1), swine influenza virus strain A/Swine/Tennessee/24/77 (H1N1), swine influenza virus strain A/Swine/Ontario/2/81 (H N1), swine influenza virus strain A/Swine/Wisconsin/1/67 (H1N1), swine influenza virus strain A/Swine/Italy/1521/98 (H1N2), swine influenza virus strain A/Swine/Italy/839/89 (H1N1), swine influenza virus strain A/Swine/Hong Kong/126/82 (H3N2), influenza virus strain A/Idaho/4/95 (H3N2), influenza virus strain A/Johannesburg/33/94 (H3N2), influenza virus strain A/Bangkok/1/79 (H3N2), influenza virus strain A/Udorn/72 (H3N2), influenza virus strain A/Hokkaido/2/92 (H1N1), influenza virus strain A/Thailand/KAN -1/04, influenza virus strain A/England/1/53, influenza virus strain A/Vietnam/3046/2004 (H5N1), influenza virus strain A/Vietnam/1203/2004 (H5N1), influenza virus strain A/tiger/Thailand/SPB-1 (H5N1), influenza virus strain A/Japan/305/57 (H2N2), influenza virus strain A/Adachi/2/57 (H2N2), influenza virus strain A/Camel/Mongolia/82 (H1N1), influenza virus strain A/RI/5/57 (H2N2), influenza virus strain A/Whale/Maine/1/84 (H13N9), influenza virus strainA/Taiwan 1/86 (H1N1), influenza virus strain A/Bayern/7/95 (H1N1), influenza virus strain A/USSR/90/77 (H1N1), influenza virus strain A/Wuhan/359/95 (H3N2), influenza virus strain A/Hong Kong/5/83 (H3N2), influenza virus strain A/Memphis/8/88 (H3N2), influenza virus strain A/Beijing/337/89 (H3N2), influenza virus strain A/Shanghai/6/90 (H3N2), influenza virus strain A/Akita/1/94 (H3N2), influenza virus strain A/Akita/11/95 (H3N2), influenza virus strain A/Memphis/6/90 (H3N2), influenza virus strain A/Udorn/307/72 (H3N2), influenza virus strain A/Singapore/1/57 (H2N2), influenza virus strain A/Ohio/4/83 (H1N1), influenza virus strain Madin Darby Canine Kidney (MDCK)-derived cell line, mouse-adapted influenza virus strain A/Guizhou/54/89 (H3N2 subtype), mouse-adapted influenza virus A/PR/8/34 (A/PR8), mouse-adapted influenza virus B/Ibaraki/2/85. Russian live attenuated influenza vaccine donor strains A/Leningrad/134/17/57, A/Leningrad/134/47/57, B/USSR/60/69, and A/Shanghai/2/2013 H7N9.

The present invention can be applied to all types of influenza vaccines, including, but not limited to, vaccines based on inactivated influenza virus such as split virus, and/or recombinant vaccines. The present invention can also be applied to influenza vaccines produced from various vaccine production systems including, but not limited to, egg based, plant based, and cell culture based vaccines. To generate egg based influenza vaccines, pathogen-free eggs are inoculated with seed viruses. Seed viruses may be naturally occurring viruses or recombinant viruses. After harvesting virus from allantoic fluid, HA antigens can be treated with alkylating agents as described below.

Cell culture based vaccines may include vaccines produced from animal cells, plant cells, yeast cells, viral cells, fungus or algae, or synthetic cells. Animal cells suitable for the present invention include, but are not limited to, insect cells, mammalian cells, and avian cells. Exemplary insect cells useful for producing influenza vaccines include, but are not limited to: SF cells, caterpillar cells, butterfly cells, moth cells, SF9 cells, SF21 cells, drosophila cells, S2 cells, High Five™ cells (Life Technologies), fall armyworm cells, cabbage looper cells, *Spodoptera frugiperda* cells, and *Trichoplasia ni* cells. Exemplary mammalian cells suitable for producing influenza vaccines include, but are not limited to: MRC-5 cells, WI-38 cells, CV-1 cells, COS cells, LLC-MK2 cells, 293 cells, 293T cells, MDBK cells, CHO cells, CAP® cells (CEVEC Pharmaceuticals), Madin-Darby canine kidney (MDCK) cells, VERO cells, EBx cells, monkey kidney cells, transformed human cell lines, and Per.C6 cells. Exemplary avian cells suitable for producing influenza vaccines include, but are not limited to, embryonated eggs, chicken embryo cells, duck cell lines such as EB66 (Valneva), AGE1.CR and AGE1.CR.pIX (Probiogen). Exemplary plant cells suitable for producing influenza vaccines include, but are not limited to, tobacco and corn. Exemplary yeast strains suitable for producing influenza vaccines include, but are not limited to, *Pichia pastoris* and *Kluyveromyces lactis*. Exemplary algae strains suitable for producing influenza vaccines include, but are not limited to, *Schizochytrium* sp. and *Chlamydomonas*.

In addition, influenza vaccines may be produced in whole organisms such as plants including, but not limited to, whole tobacco plants.

Influenza vaccines according to the present invention may be monovalent or multivalent. For example, influenza vaccines according to the present invention may be divalent, trivalent, or quadrivalent.

Alkylation of Influenza Hemagglutinin (HA)

According to the present invention, hemagglutinin (HA) from various influenza strains described herein may be treated with or exposed to an alkylating agent. As used herein, the term "alkylating agent" refers to any chemical or non-chemical substance capable of carrying out the transfer of an alkyl group from one molecule to another. Exemplary alkyl groups may include: an alkyl carbocation, a carbanion, a free radical, a carbine, and a methyl group. In some embodiments, alkylation encompasses methylation—the transfer of only one carbon group. Thus, in some embodiments, the term "alkylating agents" includes methylating agents. It is contemplated that treatment of HA results in alkylation or methylation of reactive cysteine groups, such as free cysteine residues (i.e., cysteine residues with free sulfhydryl groups). Without wishing to be bound by any particular theory, it is contemplated that during storage, influenza HA typically forms a rosette structure which needs to be disrupted by pre-treatment with a zwittergent to facilitate diffusion of the HA antigen and interaction with antisera to form precipitation ring during a SRID assay. A probable mechanism for the apparent loss of HA potency as measured by SRID over time is formation of intermolecular covalent cysteine bonds between proximal cysteine residues which prevents zwittergent disruption of the rosette structure during a standard SRID assay pre-treatment, resulting in restricted migration of the rosette macrostructure through the gel matrix and reduced interaction with the antisera. Alkylation or methylation of reactive cysteine groups prevents intermolecular disulfide bond formation, thereby facilitate HA antigen diffusion and interaction with antisera during a SRID assay.

Hemagglutinin (HA)

Influenza HA is a glycoprotein found on the surface of the influenza viruses. HA has two functions: 1) recognition of target vertebrate cells, through binding to sialic acid-containing receptors and 2) entry of the viral genome into the target cells, through fusion of the viral membrane with the host endosomal membrane. Influenza HA is a trimer of virus particles. Influenza HA is synthesized as HA0 by virus post-infection in cells that is cleaved by cellular proteases at the basic cleavage site into HA1 and HA2 mature forms, which is required for proper function of this surface protein and for viral life cycle. The M2 protein is an ion channel protein. The HA, NA, and M2 protein are present in the viral envelope which is derived from the host cell plasma membrane.

There are 18 known HA subtypes. Based on comparisons of amino acid sequence identity and of crystal structures, the HA subtypes have been divided into two main groups and four smaller clades. The different HA subtypes do not necessarily share strong amino acid sequence identity, but the overall 3D structures of the different HA subtypes are similar to one another, with several subtle differences that can be used for classification purposes. For example, the particular orientation of the membrane-distal subdomains in relation to a central α-helix is one structural characteristic commonly used to determine HA subtype (Russell et al., 2004, Virology, 325:287; incorporated herein by reference). HA exists in the membrane as a homotrimer of one of 18 subtypes, termed H1-H18. Only three of these subtypes (H1, H2, and H3) have thus far become adapted for human infection.

Suitable HA may be any naturally-occurring or recombinant HA including engineered HA. Suitable HA may have a wild-type, naturally-occurring sequence or modified amino acid sequence. A wide variety of HA sequences from influenza isolates are known in the art; indeed, the National Center for Biotechnology Information (NCBI) maintains a database (available through the world wide web at ncbi.nlm.nih.gov/genomes/FLU/flu) that, included over 9,500 HA sequences. Those of ordinary skill in the art, referring to this database, can readily identify sequences that are characteristic of HA polypeptides generally, and/or of particular HA polypeptides (e.g., H1, H2, H3, H4, H5, H6, H7, H8, H9, H10, H11, H12, H13, H14, H15, or H16 polypeptides); or of HAs that mediate infection of particular hosts, e.g., avian, camel, canine, cat, civet, environment, equine, human, leopard, mink, mouse, seal, stone martin, swine, tiger, whale, etc.

As non-limiting examples, HA suitable for the present invention includes, but is not limited to, an H1 protein isolated from a California or Solomon strain (such as, but not limited to, a California/07/2009 strain or a Solomon Is/03/2006 strain), a B protein isolated from a Brisbane, Florida, Ohio, Jiangsu or Hong Kong strain (such as, but not limited to, a Brisbane/60/2008 strain, a Florida/04/2006 strain, an Ohio/01/2005 strain, a Jiangsu/10/2003 strain or a Hong Kong/330/2001 strain) or an H3 protein isolated from a Victoria, Perth, Brisbane or Wisconsin strain (such as, but not limited to, a Victoria/361/2011 strain, a Perth/16/2009 strain, a Brisbane/16/2007 strain or a A/Wisconsin/67/05 strain).

HA suitable for the treatment with alkylation agents according to the present invention may be present in any form. For example, HA may be present in the form of an inactivated influenza virus, such as, for example, influenza virus inactivated by ultraviolet light or chemicals. Suitable chemicals for inactivation of influenza virus include, but are not limited to, formalin, beta-propiolactone, sodium deoxycholate, formaldehyde, and surfactant. Thus, inactivated influenza virus may be an inactivated whole virus or a split virus (also referred to as split viral particles). To produce a split virus, whole virus is typically subjected to disruption with detergent to solubilize the viral membrane. Chemicals used for splitting include but are not limited to: non-ionic surfactants such as octylphenol ethoxylate (Triton®, and in particular, Triton® X-100, Triton® N-101, Triton® 720 and/or Triton® X-200), sodium taurodeoxycholate, nonylphenol ethoxylate, cetyltrimethylammonium bromide (CTAB), and sodium deoxycholate.

In some embodiments, HA suitable for the present invention may be purified or partially purified. For example, HA may be in the form of a purified surface antigen or a purified or isolated HA polypeptide produced using standard recombinant technology. In some embodiments, to produce purified HA antigens, the internal subviral core of the virus is separated from the surface proteins on the basis of their differing sedimentation rates.

Alkylating Agents

Various alkylating agents may be used to stabilize influenza HA. In general, alkylation is the transfer of an alkyl group, including a methyl group, from one molecule to another. According to the present invention, an alkylating agent transfers an alkyl group (including a methyl group) to free thiols of the cysteine residues that present in influenza HA. An alkyl group may be transferred as an alkyl carbocation, a free radical, a carbanion or a carbene (or their equivalents).

Thus, an alkylating agent suitable for the present invention may be any compound capable of alkylating cysteine sulfhydryl groups. Exemplary alkylating agents suitable for the present invention include, but are not limited to, 2-iodoacetamide (IOAM), iodoacetic acid, 2-bromoacetamide, glutathione bromoacetamide, bromoacetic acid, 1,3-propane sultone, methyl methanethiosulfonate, methoxycarbonylmethyl disulfide, maleamide, maleimide-PEG, vinylpyridine, n-ethylmalemide (NEM), tosylacetamide, and any combinations thereof. In some embodiments, a suitable alkylating agent for the present invention is 2-iodoacetamide (IOAM).

Alkylation of Hemagglutinin

Figure 2:
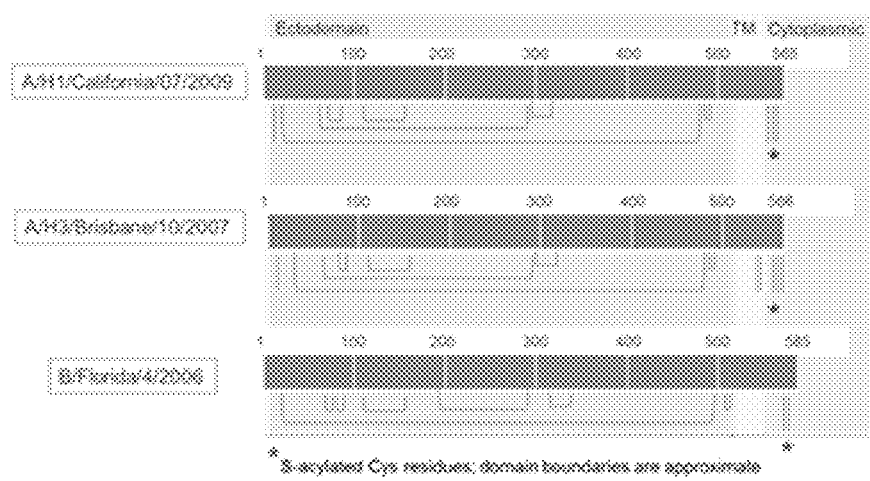
FIG. 2 depicts exemplary data illustrating that cysteine residues are highly conserved among HA strains by bioinformatics analysis.
Figure 3:
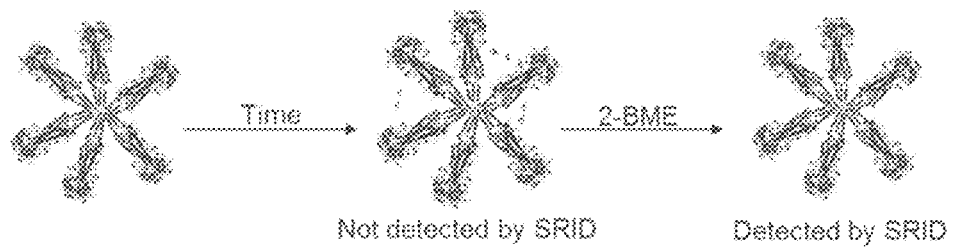
FIG. 3 depicts an exemplary scheme illustrating the involvement of cysteine in HA potency loss due to HA rosette formation.

As described in the Examples section, the inventors of the present application discovered that the loss of free thiol over time correlates well with the loss of HA potency measured by SRID. See, FIG. 1. The present inventors also discovered, by bioinformatics analysis of all WHO recommended influenza strains from 2000-2012, that cysteine residues are highly conserved. See FIG. 2. In H1 and B strains, 16 cysteine residues are present in HA with conserved locations, whereas in the H3 strains, 18 cysteine residues are present also with conserved locations. Typically, as shown in FIG. 2, most of these residues exist as di-sulfide bonds. However, 3-5 (depending on the subtype) are found unpaired, particularly, in the transmembrane and cytoplasmic domains. Some or all of the unpaired cysteine residues may be acetylated during expression. However, a process of viral inactivation, in particular, viral splitting using surfactant, may cause acetylated cysteine residues to become inappropriately reactive, e.g., to form undesired bonds with other free cysteine residues in the vicinity. In addition, other methods used during vaccine production process may also cause acetylated cysteine residues to become inappropriately reactive. It is also possible that a di-sulfide bond may be reduced during the manufacturing process such that originally paired cysteine residues become reactive. Thus, influenza HA typically contains up to 5 free cysteine residues, depending on strain types. Specifically, influenza HA may contain 1, 2, 3, 4, or 5 free cysteine residues. However, under some circumstance, influenza HA may contain up to 16 or 18 free cysteine residues, depending on strain types. Specifically, influenza HA may contain 5, 6, 7, 8, 9, 10, 11, 12, 13, 14, 15, 16, 17 or 18 free cysteine residues.

HA antigens can be alkylated at any time point during the influenza vaccine manufacturing process. In other words, an alkylating agent can be added to stabilize HA antigens at any point during the influenza vaccine manufacturing process. For egg based influenza virus, typically, the virus is harvested by removing allantoic fluid from an egg. The fluid is centrifuged to remove cellular debris. Whole virus purification, concentration and inactivation follows next. Methods such as column chromatography or zonal centrifugation on a density gradient purifies the virus. In some embodiments, inactivation with chemicals or agents takes place next. Chemicals used for inactivation include, but are not limited to: formaldehyde, sodium deoxycholate, betapropiolactone and formalin. In addition, virus can also be inactivated with ultraviolet light. To produce the split virus or subunit vaccines, whole virus is subjected to disruption with detergent to solubilize the viral membrane. Suitable chemicals used for splitting include but are not limited to: non-ionic surfactants such as octylphenol ethoxylate (Triton® X-100), sodium taurodeoxycholate, nonylphenol ethoxylate, cetyltrimethylammonium bromide (CTAB), and sodium deoxycholate. With split virus vaccines, the choice and use of surfactant ensures that the subviral core itself is disassembled. For subunit vaccines the internal subviral core of the virus is separated from the surface proteins on the basis of their differing sedimentation rates.

In some embodiments, the inactivated/split virus is further purified and then suspended in sodium phosphate buffered isotonic sodium chloride solution. Typically, diafiltration is used to remove surfactant and other media or chemical components from the production and processing, terminating in a sterile filtration step to yield a monovalent bulk solution.

An alkylating agent may be added prior to, during or after upstream influenza virus production and processing, harvest, splitting, concentration, clarification, inactivation, diafiltration, and/or formulation.

In some embodiments, an alkylating agent is added after splitting the virus. An exemplary scheme incorporating the step of alkylating agent (e.g., IOAM) treatment is shown in FIG. 7.

Typically, alkylation of HA can be carried out by incubating the HA with an alkylating agent at a pre-determined temperature for a period of time. In some embodiments, HA and an alkylating agent are incubated at a temperature of or less than about 37° C. (e.g., of or less than about 30° C., 25° C., 20° C., 15° C., 10° C., or 5° C.). In some embodiments, HA and an alkylating agent are incubated at a temperature ranging between about 0-5° C., 2-8° C., 5-10° C., 10-15° C., 15-20° C., 20-25° C., 25-30° C., or 30-37° C. In some embodiments, HA and an alkylating agent are incubated at room temperature (also referred to as ambient temperature). In some embodiments, HA and an alkylating agent are incubated at storage temperature (e.g., about 0-5° C., about 2-8° C., or about 0-10° C.).

HA and an alkylating agent may be incubated for any period of time. In some embodiments, HA and an alkylating agent are incubated for up to about 24 hours, about 20 hours, about 18 hours, about 16 hours, about 14 hours, about 12 hours, about 10 hours, about 8 hours, about 6 hours, about 4 hours, about 2 hours, about 1.5 hours, about 1 hour, about 50 minutes, about 40 minutes, about 30 minutes, about 20 minutes, about 10 minutes, or about 5 minutes. In some embodiments, HA and an alkylating agent are incubated for at least about 1 minutes, about 5 minutes, about 10 minutes, about 30 minutes, about 1 hour, about 1.5 hours, about 2 hours, about 3 hours, about 4 hours, about 5 hours, about 6 hours, about 8 hours, about 10 hours, about 12 hours, about 14 hours, about 16 hours, about 18 hours, about 20 hours, or about 24 hours. In some embodiments, HA and an alkylating agent are incubated for about 0-2 hours, about 0-1.5 hours, about 0-1 hour, about 0.1-5.0 hours, about 0.1-4 hours, about 0.1-3 hours, about 0.1-2 hours, about 0.1-1 hours, about 0.1-0.5 hours, about 0.5-3 hours, or about 0.5-2 hours.

HA and an alkylating agent may be present at a range of relative concentrations. For example, an alkylating agent may be present at a concentration of more than 1X molar excess to HA-cysteine concentration (e.g., more than 2X, 3X, 4X, 5X, 10X, 15X, 20X, 25X, 30X, 35X, 40X, 45X, 50X, 55X, 60X, 65X, 70X, 75X, 80X, 85X, 90X, 95X, or 100X molar excess to HA-cysteine concentration). In some embodiments, an alkylating agent may be present at a concentration ranging from 1X to 100X, from 1X to 90X, from 1X to 85X, from 1X to 75X, from 1X to 50X, from 5X to 85X, from 5X to 80X, from 5X to 75X, from 5X to 50X, from 5X to 40X, from 5X to 30X, from 5X to 20X, or from 5X to 10X molar excess to HA-cysteine concentration.

In some embodiments, an alkylating agent may be present at a concentration ranging from about 1 mM-1 M, 1 mM-900 mM, 1 mM-800 mM, 1 mM-700 mM, 1 mM-600 mM, 1 mM-500 mM, 1 mM-400 mM, 1 mM-300 mM, 1 mM-200 mM, 1 mM-100 mM, 1 mM-50 mM, 5 mM-1 M, 10 mM-900 mM, 20 mM-800 mM, 30 mM-700 mM, 40 mM-600 mM, 50 mM-500 mM, 60 mM-400 mM, 70 mM-300 mM, 80 mM-200 mM, 90 mM-100 mM, 10 mM-50 mM, 10 mM-100 mM, 10 mM-500 mM, 50 mM-1,000 mM, 100 mM-900 mM, 200 mM-800 mM, or 300 mM-700 mM. In some embodiments, an alkylating agent may be present at a concentration ranging from about 1 μg/ml-1,000 μg/ml, 1 μg/ml-900 μg/ml, 1 μg/ml-800 μg/ml, 1 μg/ml-700 μg/ml, 1 μg/ml-600 μg/ml, 1 μg/ml-500 μg/ml, 1 μg/ml-400 μg/ml, 1 μg/ml-300 μg/ml, 1 μg/ml-200 μg/ml, 1 μg/ml-100 μg/ml, 5 μg/ml-50 μg/ml, 5 μg/ml-100 μg/ml, 5 μg/ml-200 μg/ml, 5 μg/ml-300 μg/ml, or 5 μg/ml-500 μg/ml, 10 μg/ml-1,000 μg/ml, 20 μg/ml-900 μg/ml, 30 μg/ml-800 μg/ml, 40 μg/ml-700 μg/ml, 50 μg/ml-600 μg/ml, 60 μg/ml-500 μg/ml, 70 μg/ml-400 μg/ml, 80 μg/ml-300 μg/ml, or 90 μg/ml-200 μg/ml. In some embodiments, an alkylating agent may be present at a concentration of or greater than about 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 20 mM, 30 mM, 40 mM, 50 mM, 100 mM, 200 mM, 300 mM, 400 mM, or 500 mM. In some embodiments, an alkylating agent may be present at a concentration of or greater than about 1 μg/ml, 2 μg/ml, 3 μg/ml, 4 μg/ml, 5 μg/ml, 6 μg/ml, 7 μg/ml, 8 μg/ml, 9 μg/ml, 10 μg/ml, 11 μg/ml, 12 μg/ml, 13 μg/ml, 14 μg/ml, 15 μg/ml, 20 μg/ml, 30 μg/ml, 40 μg/ml, 50 μg/ml, 60 μg/ml, 70 μg/ml, 80 μg/ml, 90 μg/ml, 100 μg/ml, 200 μg/ml, 300 μg/ml, 400 μg/ml, or 500 μg/ml.

In some embodiments, the alkylating agent is removed from the treated vaccine composition to ensure that the final drug substance is substantially free of the alkylating agent. Any method may be used to remove the alkylating agent. In some embodiments, the alkylating agent is removed by dialfiltration. Depending on the molecular weight of the alkylating agent, a filter with an appropriate cut-off size may be used.

Typically, diafiltration is used to remove surfactant and other media components or chemical compounds from the upstream process to purify and/or concentrate HA antigens. In some embodiments, a diafiltration step is carried out following an inactivation step (e.g., FIG. 7). Typically, an inactivating agent (e.g., formalin, beta-propiolactone, sodium deoxycholate, or formaldehyde) is added during the inactivation step prior to diafiltration. In some embodiments, an alkylating agent is removed together with an inactivating agent added during the inactivation step to ensure process efficiency. Thus, in some such embodiments, an alkylating agent is added prior to or simultaneously with the addition of an inactivating agent (e.g., formalin, beta-propiolactone, sodium deoxycholate, or formaldehyde). In some embodiments, an alkylating agent is added about 30 minutes, 1 hour, 1.5 hours, 2 hours, 2.5 hours, 3 hours, 3.5 hours, 4 hours, 4.5 hours, 5 hours, 5.5 hours or 6 hours prior to the addition of an inactivating agent (e.g., formalin, beta-propiolactone, sodium deoxycholate, or formaldehyde).

Different levels of alkylation of HA antigens can be achieved with the methods of the present invention. In general, treating HA antigens with alkylating agents results in alkylation of one or more cysteine residues of HA. In some embodiments, treating HA antigens with alkylating agents results in alkylation of 1-5, 1-4, 1-3 or 1-2 cysteine residues. In particular embodiments, treating HA antigens with alkylating agents results in alkylation of 1, 2, 3, 4, or 5 cysteine residues. Depending on the number of free cysteine residues in the starting HA antigens, in some embodiments, treating HA antigens with alkylating agents can result in alkylation of up to 16 or 18 cysteine residues. More specifically, treating HA antigens with alkylating agents can result in alkylation of up to 5, 6, 7, 8, 9, 10, 11, 12, 13, 14, 15, 16, 17 or 18 cysteine residues. In some embodiments, treating HA antigens with alkylating agents results in alkylation of about 1-100%, 1-90%, 1-80%, 1-70%, 1-60%, 1-50%, 1-40%, 1-30%, 1-20%, or 1-10% cysteine residues. In some embodiments, treating HA antigens with alkylating agents results in alkylation of or greater than about 10%, 20%, 30%, 40%, 50%, 60%, 70%, 80%, or 90% cysteine residues. In some embodiments, treating HA antigens with alkylating agents results in alkylation of substantially all free cysteine residues. In various embodiments, treating HA antigens with alkylating agents according to the present invention does not result in non-specific alkylation. As described above, alkylation as used herein encompasses methylation. In some embodiments, treating HA antigens with alkylating agents according to the present invention does not result in ubiquitous methylation.

Methods of measuring alkylation levels are well known in the art. In some embodiments, the alkylation level described herein is measured by reduced level of free cysteine residues. Exemplary methods of measuring alkylation levels or reduced level of free cysteine residues are described in the Examples section and various additional methods are known in the art and can be used to practice the present invention. For example, sodium dodecyl sulfate-polyacrylamide gel electrophoresis (SDS-PAGE) under non-reducing conditions can detect large changes in protein mass and disulfide cross-links. Mass spectrometry may be used to determine the level of alkylation by detecting the changes of protein mass. Peptide mapping combined with mass spectrometry may be used to characterize alkylations of specific cysteine residues. For example, an HA protein may be first digested with one or more enzymes to produce a specific set of peptides based on the cleavage sites in the primary sequence. These peptides can then be analyzed by mass spectrometry directly (i.e. matrix-assisted laser desorption ionization-time of flight mass spectrometry (MALDI-TOF) or after chromatographic separation (i.e. liquid-chromatography-mass spectrometry, LC-MS). Changes in the mass to charge ratio (m/z) of the peptides can be indicative of alkylation (Biotechniques. 2006; 40:790-798). In some embodiments, the alkylation level described herein may be determined by cysteine quantitation using amino acid analysis.

Measuring HA Antigen Potency Using SRID and Immunogenicity

SRID assays have been used to determine the HA content in the influenza vaccine and to measure potency of influenza virus vaccines licensed by the Food and Drug Administration for use in the United States since 1978. Specifically, SRID determines HA content in an influenza vaccine by using specific anti-HA antibodies. For example, samples of detergent solubilized vaccines are applied onto an agarose plate with a thin gel layer punctuated with, e.g., 3-4 mm holes containing a strain-specific antiserum. Dilutions of standard HA antigen are placed into the wells alongside samples with unknown antigen concentrations. The plates are typically incubated in a moist chamber at room temperature to allow diffusion of the antigen. Reaction of the antigen with the antibody produces a zone of precipitation (which is in form of precipitation ring). In some embodiments, the resulting rings of antigen:antibody precipitate are enhanced with Coomassie blue stain. The amount of HA in the vaccine samples can be quantified by comparing the ring diameters of samples with the diameters of known concentrations of the reference HA antigen. A potency value for the vaccine tested can be obtained based on the amount of HA. In some embodiments, a potency value measured by a SRID assay is also referred to as apparent potency or apparent stability.

The present invention provides influenza vaccines with reduced potency loss as measured by SRID. In some embodiments, treatment with alkylating agents according to the present invention results in reduced apparent potency loss of the influenza vaccine determined by SRID as compared to an otherwise identical influenza vaccine without the treatment of the alkylating agent. For example, treatment with alkylating agents according to the present invention may result in reduced apparent potency loss of the influenza vaccine determined by SRID by at least about 10%, 20%, 30%, 40%, 50%, 60%, 70%, 80%, 90%, 1-fold, 2-fold, 3-fold, 4-fold or 5-fold as compared to an otherwise identical influenza vaccine without the treatment of the alkylating agent.

Thus, influenza vaccines containing HA antigens treated with or exposed to alkylating agents according to the present invention are characterized with remarkable stability and significantly reduced potency loss after short or long term storage under standard conditions. In some embodiments, influenza vaccines containing HA antigens treated with or exposed to alkylating agents have no more than about 50% (e.g., no more than 40%, 30%, 20%, 10%, 5%, or 1%) apparent potency loss determined by SRID after short or long term storage under standard conditions. In some embodiments, influenza vaccines containing HA antigens treated with or exposed to alkylating agents have no more than about 10% (e.g., no more than about 9%, 8%, 7%, 6%, 5%, 4%, 3%, 2%, or 1%) apparent HA potency loss determined by SRID after short or long term storage under standard conditions. In some embodiments, influenza vaccines containing HA antigens treated with or exposed to alkylating agents have no more than about 1% (e.g., no more than about 0.9%, 0.8%, 0.7%, 0.6%, 0.5%, 0.4%, 0.3%, 0.2%, or 0.1%) apparent HA potency loss determined by SRID after short or long term storage under standard conditions. In some embodiments, influenza vaccines containing HA antigens treated with or exposed to alkylating agents have substantially no apparent HA potency loss determined by SRID after short or long term storage under standard conditions. In various embodiments, the apparent HA potency loss may be determined after a short term storage under standard conditions. Exemplary short term storage under standard conditions includes a storage at 1-30° C., 1-25° C., 1-20° C., 1-15° C., 1-10° C., 1-5° C., 2-10° C., 2-8° C., 2-6° C., 2-4° C., 10-30° C., 10-25° C., 10-20° C., 15-25° C., 15-20° C., 20-25° C., or room temperature for up to 30 days, 60 days, or 90 days. In various embodiments, the apparent HA potency loss may be determined after a long term storage under standard conditions. Exemplary long term storage under standard conditions includes a storage at 1-30° C., 1-25° C., 1-20° C., 1-15° C., 1-10° C., 1-5° C., 2-10° C., 2-8° C., 2-6° C., 2-4° C., 10-30° C., 10-25° C., 10-20° C., 15-25° C., 15-20° C., 20-25° C., or room temperature for more than 3 months, 4 months, 5 months, 6 months, 7 months, 8 months, 9 months, 10 months, 11 months, 12 months, 1.5 years, 2 years, 2.5 years, 3 years, 3.5 years, 4 years, 4.5 years or 5 years.

It is contemplated that influenza vaccines containing HA antigens treated with or exposed to alkylating agents according to the present invention are further characterized by having at least comparable immunogenicity and improved potency as measured by SRID as compared to otherwise identical influenza vaccines without the treatment of or exposure to the alkylating agents. Various methods for measuring immunogenicity are known in the art and can be used to practice the present invention. For example, the immunogenicity of HA antigens may be tested by in vitro assays, including, but not limited to: ELISA and T-cell assays. In some embodiments, the immunogenicity of HA antigens may be tested by administering HA antigens to animal subjects and measuring the ability to elicit neutralizing antibody response in vivo. Animal models for testing the immunogenicity of HA antigens include, but are not limited to: mice, rats, ferrets, swine, birds, bats, and non-human primates. In some embodiments, the immunogenicity of HA antigens may be tested by administering HA antigens to human patients.

Immunogenic Vaccine Compositions

Alkylated HA antigens according to the present invention can be formulated to form immunogenic compositions of influenza vaccines. An alkylated HA antigen may be formulated alone or in combination with other stabilized or unstabilized influenza antigens from same or different influenza strains. Thus, immunogenic compositions of the present invention may be monovalent or multivalent (e.g., divalent, trivalent, or quadrivalent).

Immunogenic compositions of the invention can contain additional substances, such as adjuvants to enhance the effectiveness of the vaccines, and pharmaceutically acceptable carriers including, but not limited to, wetting or emulsifying agents, or buffering agents (Remington's Pharmaceutical Sciences, 18th edition, Mack Publishing Company, (ed.) 1980).

Suitable adjuvants may include, but are not limited to, mineral salts (e.g., $AlK(SO_4)_2$, $AlNa(SO_4)_2$, $AlNH(SO_4)_2$, silica, aluminum, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34th Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from *Mycobacterium tuberculosis*, substances found in *Cornyebacterium parvum*, *Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8); the CCR5 inhibitor CMPD167 (see Veazey, R. S. et al (2003) J. Exp. Med. 198: 1551-1562); and Squalene emulsion, i.e., MF59.

Adjuvant widely used in humans has been aluminum. In some embodiments, a suitable adjuvant is aluminum phosphate. In some embodiments, a suitable adjuvant is aluminum hydroxide. In some embodiments, a suitable adjuvant is a combination of aluminum phosphate and aluminum hydroxide. Saponin and its purified component Quil A, Freund's complete adjuvant and other adjuvants are typically used in research and veterinary applications; however, new chemically defined preparations such as muramyl dipeptide, monophosphoryl lipid A, phospholipid conjugates such as those described by Goodman-Snitkoff et al. J. Immunol. 147:410-415 (1991) and incorporated by reference herein, encapsulation of the protein within a proteoliposome as described by Miller et al., J. Exp. Med. 176: 1739-1744 (1992) and incorporated by reference herein, and encapsulation of the protein in lipid vesicles such as NOVASOME™ lipid vesicles (Micro Vescular Systems, Inc., Nashua, N.H.) should also be useful for human administration.

Typically, immunogenic vaccine compositions according to the present invention include a pharmaceutically acceptable carrier. In general, pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

Pharmaceutically acceptable carriers are determined in part by the particular composition being administered, as well as by the particular method used to administer the composition. Accordingly, there is a wide variety of suitable formulations of immunogenic compositions of the present invention.

Immunogenic vaccine compositions of the present invention can be administered to a subject by any of the routes normally used for introducing influenza vaccines into a subject. Methods of administration include, but are not limited to, intradermal, intramuscular, intraperitoneal, parenteral, intravenous, subcutaneous, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, and tablets of the kind previously described. Administration can be systemic or local.

In some embodiment, an immunogenic vaccine composition is formulated for parenteral (i.e., intramuscular, intradermal or subcutaneous) administration or nasopharyngeal (i.e., intranasal) administration. Typically, formulations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the immunogenic compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose administered to a subject in the context of the present disclosure should be sufficient to induce a beneficial therapeutic response in a subject over time, or to inhibit or prevent influenza virus infection. The dose required will vary from subject to subject depending on the species, age, weight and general condition of the subject, the severity of the infection being treated, the particular composition being used and its mode of administration. An appropriate dose can be determined by one of ordinary skill in the art using only routine experimentation.

Immunogenic compositions of the invention can be appropriately applied to prevent diseases as prophylactic vaccination or treat diseases as therapeutic vaccination. Beyond the human vaccines described, the compositions and methods of the invention can be used to immunize animal stocks. The term animal means all animals including humans. Examples of animals include humans, cows, dogs, cats, goats, sheep, horses, pigs, turkeys, ducks, chickens, etc. Since the immune systems of all vertebrates operate similarly, the applications described can be implemented in all vertebrate systems.

Although the present invention and its advantages have been described in detail, it should be understood that various changes, substitutions and alterations can be made herein without departing from the spirit and scope of the invention as defined in the appended claims.

The invention will be more fully understood by reference to the following examples. They should not, however, be construed as limiting the scope of the invention. All literature citations are incorporated by reference.

EXAMPLES

Example 1

Characterization of Influenza Vaccine Potency Loss Measured by SRID

This example describes experiments conducted to characterize and understand mechanism behind the poor stability profile of influenza hemagglutinin (HA) potency measured by Single Radial Immunodiffusion (SRID). As shown below, the experiments described herein demonstrated a correlation between the loss of potency measured by SRID and a decrease in free thiols in HA.

Specifically, this example explores the factors responsible for the loss in potency seen in HA antigens. A reversed phase high performance liquid chromatography (RP-HPLC) assay demonstrated that over the same period where SRID indicates significant loss of HA potency, no decrease in total HA content occurred. A supporting observation was made for samples treated with 2-mercaptoethanol (BME) prior to SRID analysis. For these pre-treated samples, no loss in potency was observed. These observations indicate that while HA potency as measured by SRID declines over time, the overall HA content does not change. This same phenomena was also observed for multivalent drug product Subsequently, analysis of free thiol was evaluated with respect to time. As demonstrated in FIG. 1, it was found that the loss of free thiol signal over time correlates well with the loss of HA potency by SRID in various influenza vaccines based on different strains. These observations suggest the involvement of disulfide bond formation in the mechanism for the apparent decrease in HA potency.

Conserved features among the HA antigens of all influenza strains were then investigated. Cysteines are a likely source of free thiols in HA antigens. To better understand the presence and role of HA cysteine residues, a bioinformatics survey of all WHO recommended influenza strains from 2000-2012 was conducted (see FIG. 2). This work demonstrated that cysteine residues are entirely conserved among subtypes, and differences were noted only for the H3 strain relative to the H1 and B strains. In H1 and B strains, 16 cysteine residues were identified with conserved locations, whereas in the H3 strain, 18 cysteine residues were identified, also with conserved locations. The majority of these residues exist as disulfide bonds of known pairs, with just 3-5 residues (depending on the subtype) unpaired in the transmembrane and cytoplasmic domains. While these residues would be expected to be acetylated and thus, unable to form disulfide bonds during expression, it is possible that the process of viral splitting using, for example, Triton® X-100 causes them to become reactive and form additional disulfide bonds.

Without wishing to be bound by any particular theory, it is contemplated that the involvement of cysteine in HA potency loss relates to their role in HA rosette formation. HA rosette formation is mediated by the hydrophobic nature of the transmembrane and cytoplasmic domains. In rosette form, HA monomers are in close contact, which facilitates intermolecular covalent bond formation. Based on this information, the probable mechanism for the loss of HA potency over time is the formation of intermolecular covalent cysteine bonds which prevent zwittergent disruption of the rosette structure during the standard SRID analysis pretreatment. The result is restricted migration of the rosette macrostructure through the gel matrix and reduced interaction with the antisera. See FIG. 3. Over time, the cysteine residues in the HA antigens form intermolecular bonds that lock the rosette structures together and cause hindered movement of the HA antigens through SRID gels.

Example 2

Treatment with Alkylating Agent Reduced Apparent HA Potency Loss

This example demonstrated that treatment of influenza vaccines with an alkylating agent results in the stabilization or reduction of the loss of HA potency as measured by SRID.

Figure 4:
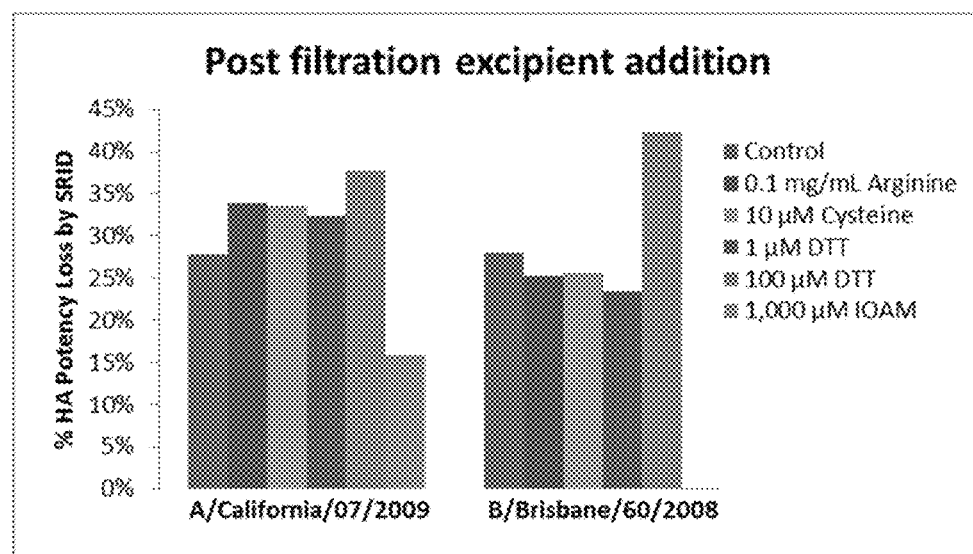
FIG. 4 depicts exemplary data illustrating HA potency loss after addition of different GRAS excipients, reducing agents and an alkylating agent, 2-iodoacetamide (IOAM).

The mechanistic understanding described in Example 1 prompted stability studies of drug substance spiked with various GRAS (generally recognized as safe) excipients, several reducing agents, and one common alkylating/methylating agent: 2-Iodoacetamide (IOAM). After filtration, HA antigens from A/California or B/Brisbane were exposed to control vehicle, 0.1 mg/mL arginine, 10 uM cysteine, 1 uM DTT, 100 uM DTT, and 1000 uM IOAM, respectively, and then tested via the SRID assay. The overall objective was to slow the loss of SRID-measured potency, and exemplary results of the study are depicted in FIG. 4. Surprisingly, only the addition of IOAM stabilized the apparent HA potency loss.

Figure 5:
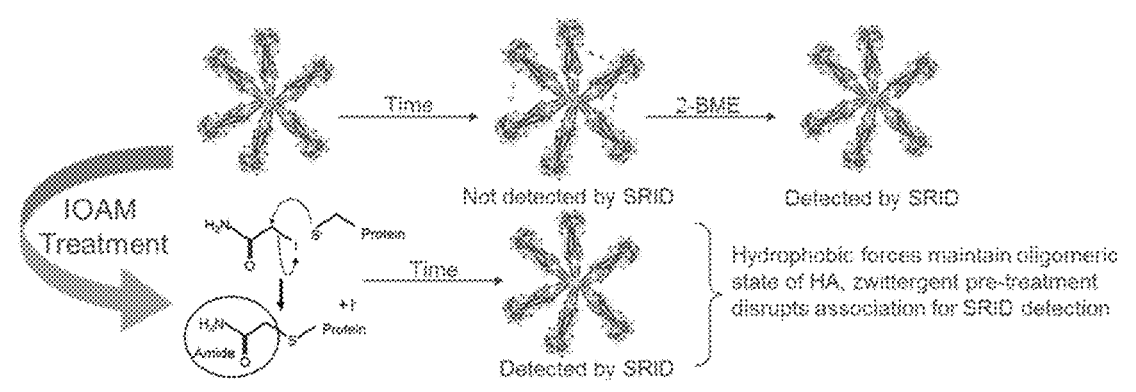

It is contemplated that the stabilization of HA potency observed in this study is caused by alkylation of reactive cysteine groups which precludes intermolecular disulfide bond formation. Iodine acts as an excellent leaving group, making nucleophilic attack of the reactive cysteine on IOAM a favorable reaction. An exemplary mechanism is illustrated in FIG. 5.

Example 3

Addition Point of IOAM during Influenza Vaccine Manufacturing Process

This example summarized the experiments designed to identify the proper addition point of an alkylating agent such as IOAM during the manufacturing process to optimize stabilizing effects, reduce cost, and facilitate clinical testing.

The primary development studies focused on identifying the proper addition point of the monovalent drug substance manufacturing process to expose HA to an alkylating agent such as IOAM. Early studies had been performed through addition of IOAM directly to the final drug substance; however it is desirable to remove residuals of the alkylating agent for clinical use. This could be achieved via diafiltration given the low molecular weight of IOAM. However, it is desired to avoid addition of a second diafiltration to the process to prolong the lot processing time. As such, the addition was targeted to occur upstream of the existing diafiltration and concentration step. Given the similarity of the chemistry to formalin inactivation, the first preference was to add IOAM and formalin simultaneously such that the length of the process was not impacted. However, when samples were processed with both concurrent alkylation and inactivation versus successive alkylation and inactivation, results varied.

Figure 6:
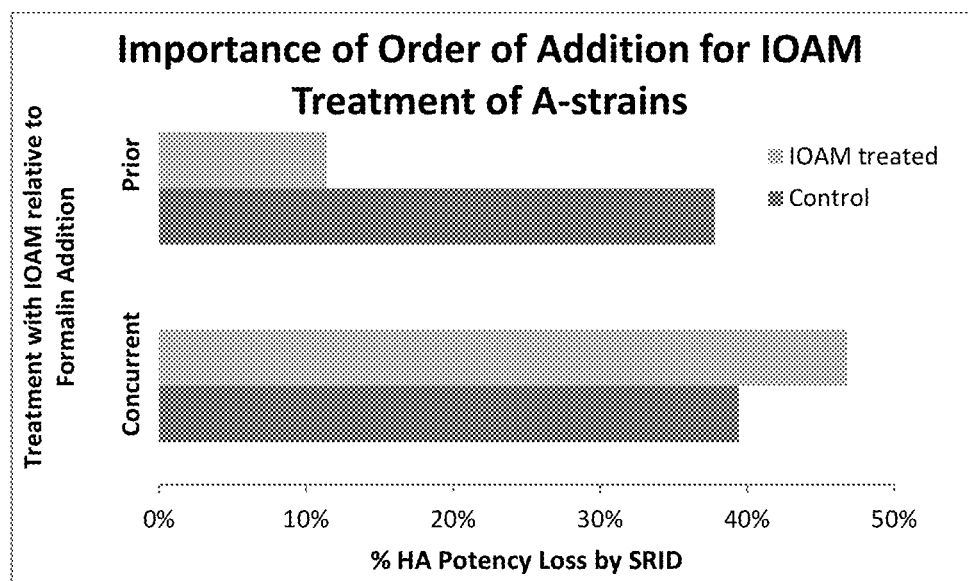
FIG. 6 depicts exemplary data illustrating that the order of IOAM addition may be important in certain strains.

Following these observations, the process was modified to include incubation with IOAM for two hours prior to the addition of formalin. Exemplary results showing the impact of order of IOAM addition on A-strain potency are depicted in FIG. 6.

Figure 7:
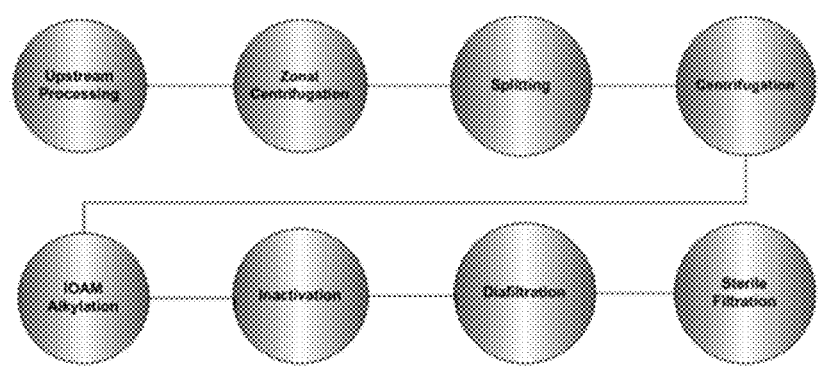
FIG. 7 depicts an exemplary process for manufacturing influenza vaccine.

HA antigens may display different levels of stabilization depending upon when the antigen is exposed to IOAM during the manufacturing process. Ideally, addition of an alkylating agent is implemented upstream of diafiltration, which allows residuals to clear leaving resulting drug substance free of the alkylating agent (e.g., IOAM) related residuals. An exemplary influenza manufacturing process is shown in FIG. 7.

Example 4

Optimal Concentration Range of IOAM for HA Stabilization

This example explores the optimal concentration ranges of IOAM to stabilize HA potency, in particular, the concentration ranges of IOAM that stabilizes HA without allowing non-specific alkylation.

Figure 8:
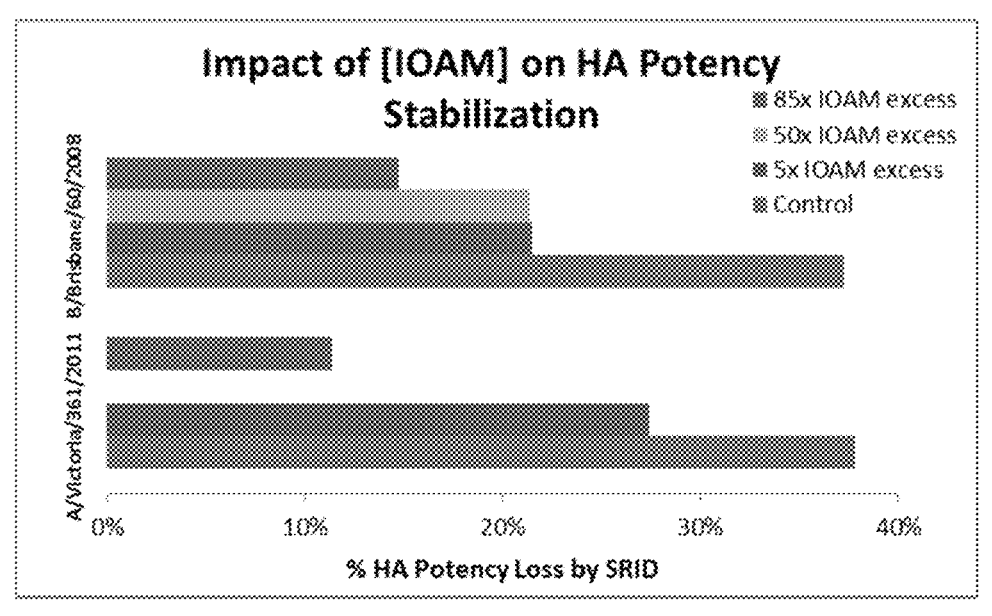

This was done by selecting a range of IOAM concentrations and evaluating the resulting HA potency stabilization and then cross referencing this information with overlays of the amino acid analysis for each concentration studied. The IOAM concentration range was set at 5×, 50× and 85× molar excess of IOAM to HA-cysteine concentration in this study. As shown in FIG. 8, the B/Brisbane strain was substantially stabilized at all three IOAM levels, and no differences outside of the 14% SRID variability criteria were observed despite the visual trend. For A/Victoria, the 50× level was not tested in this study; however a difference was noted between the 5× and 85× levels with the higher 85× level resulted in lower potency loss. The results indicate that a broad concentration range of an alkylating agent may be used to stabilize HA potency.

Figure 9:
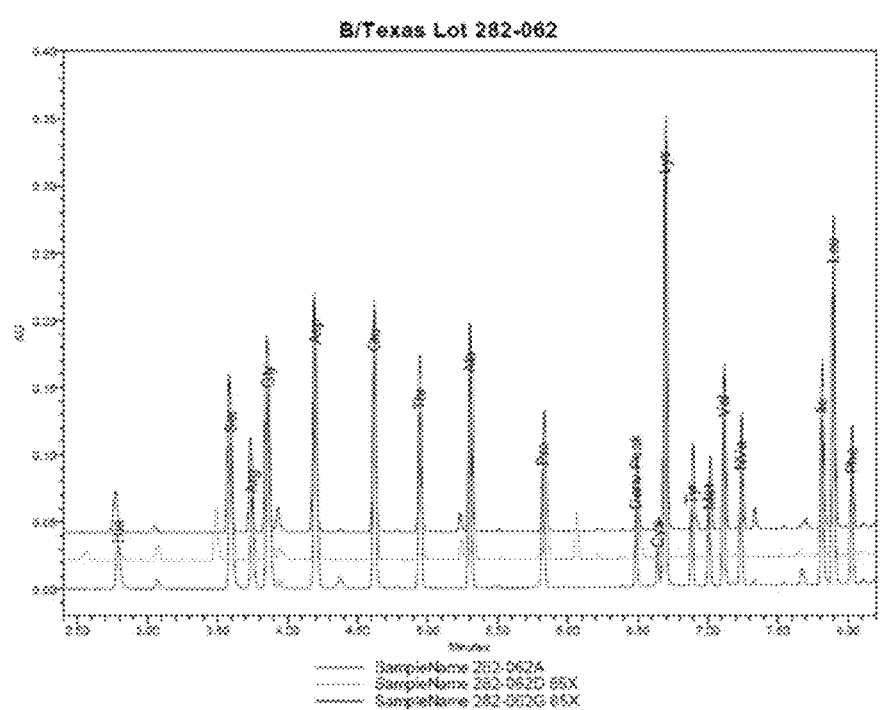
FIG. 9 depicts an exemplary amino acid analysis result of IOAM treated samples. The D arm had IOAM left in the sample while the G arm had IOAM removed.

The amino acid alkylation or methylation status after IOAM treatment was then analyzed. Specifically, samples were acid hydrolyzed and then separated using RP-HPLC employing pre-column derivatization for UV detection. Exemplary amino acid analysis for the IOAM treated samples is depicted in FIG. 9. As can be seen, the data for the IOAM treated samples mimics the control sample, and did not contain any new peaks which would indicate ubiquitous methylation. Unfortunately, cysteine residues were not stable throughout this analysis, and as such are not well enough recovered to monitor their alkylation using these particular hydrolysis conditions. Further development of the assay has resulted in hydrolysis conditions for which cysteine residues can be monitored.

Example 5

Quantification of Cysteines in Influenza Vaccines Treated by IOAM

This example demonstrates that influenza vaccines treated with an alkylating agent (e.g., IOAM) contain reduced level of free cysteines as compared to untreated control.

Figure 10:
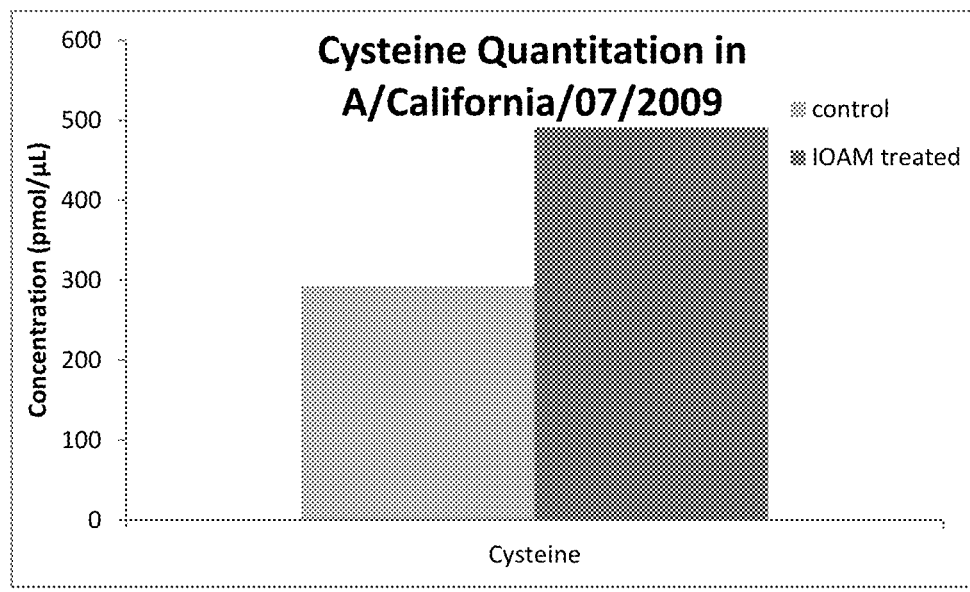
FIGS. 10 and 11 depict exemplary quantification results of concentration of free cysteine in influenza vaccines treated by IOAM compared to untreated samples.

Specifically, the concentration of free cysteines were measured for IOAM treated HA antigens from the A/California strain and compared to untreated control. In this assay, proteins were first degraded to free amino acids by acid hydrolysis under vacuum and heat (e.g., 150° C.) for about one hour. The amino acids were derivatized using the Waters AccQ-Tag Ultra derivatization kit. The derivatives were then separated by RP-HPLC and quantified based on UV detection. Exemplary results are shown in FIG. 10. As shown in FIG. 10, samples treated with IOAM showed an approximately 30-35% reduction in free cysteine residues compared to untreated control, indicating that about 30-35% cysteine residues are alkylated in IOAM treated vaccine samples.

Figure 11:
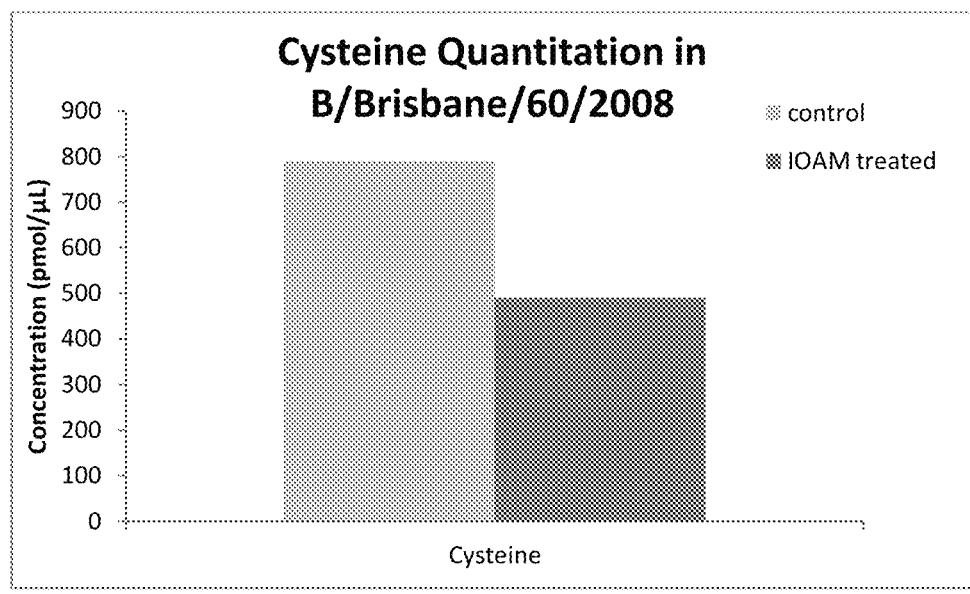

A similar experiment was done to analyze IOAM-treated B/Brisbane vaccine samples and exemplary results are shown in FIG. 11. Similar to the A/California strain, B/Brisbane samples treated with IOAM showed a roughly 30-38% reduction in free cysteine residues compared to untreated control, which again indicates that about 30-38% cysteine residues are alkylated in IOAM treated vaccine samples.

In these experiments, the IOAM treated samples shown in the A/Cal and B/Bris graphs were prepared using the 50× IOAM-HA ratio.

Example 6

Treatment with IOAM Improves Long Term Stability

This example demonstrates that treatment with an alkylating agent (e.g., IOAM) significantly improves long term stability of HA antigens in a SRID assay.

Figure 12:
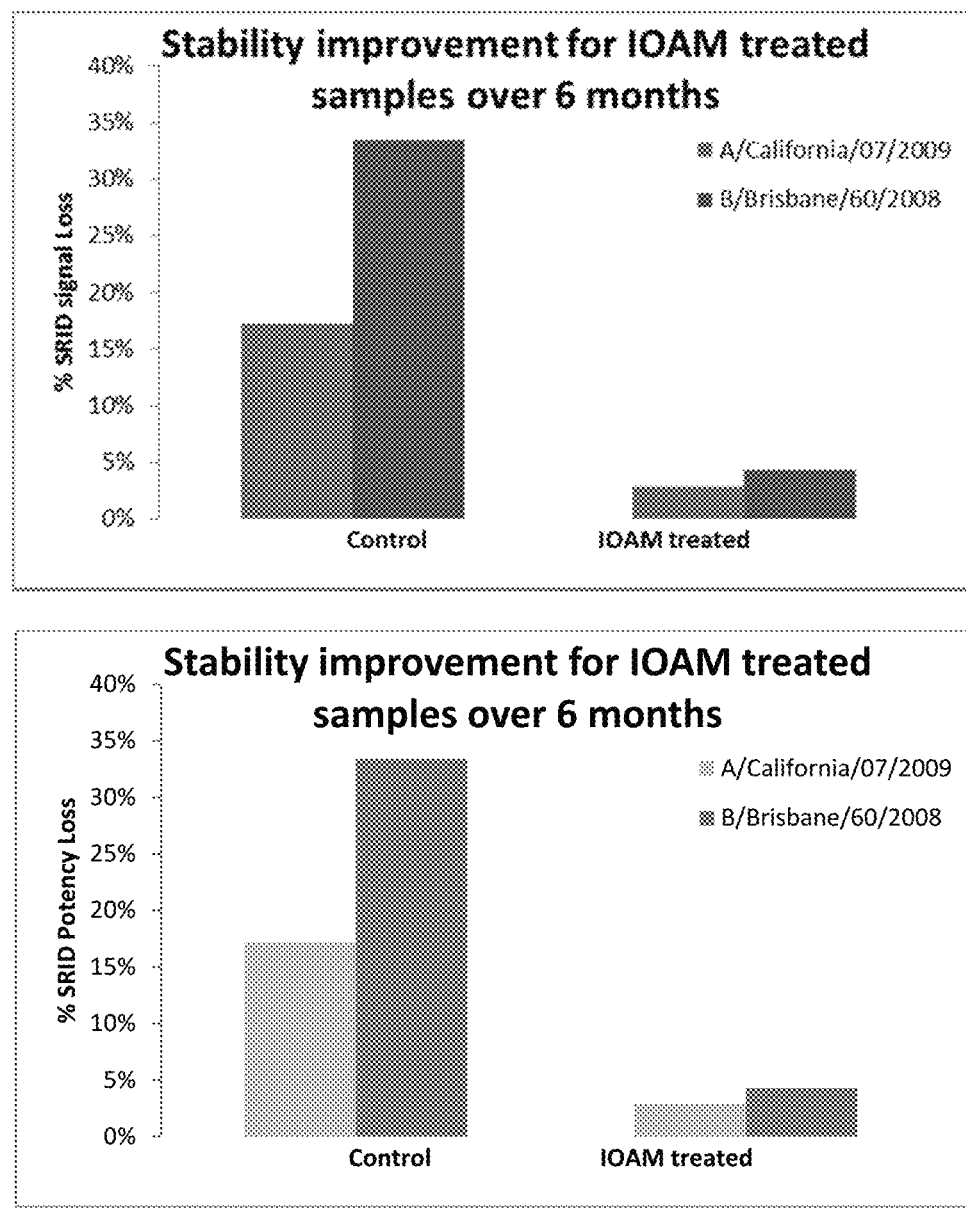
FIG. 12 depicts exemplary data illustrating 6 month HA stability results of IOAM treated vaccine samples.

The 50× IOAM concentration was chosen for this study. Exemplary 6 month HA stability results of this experiment are shown in FIG. 12. Relative to the control arms for both A/California and B/Brisbane, the IOAM treated arms were significantly more stable as measured by SRID assays). The data demonstrates that IOAM treated HA antigens are stable after 6 months with an approximately 1-5% loss in potency as measured in SRID assays.

Immunogenicity studies on IOAM treated samples were conducted using mouse model according to standard protocols. Briefly, female BALB/c mice (Harlan Laboratories) were immunized with 24, 12, 10, 3.0, 1.0, 0.30, 0.030 µg of HA/strain (determined by SRID potency) of each bivalent formulated bulk drug product containing A/California/07/2009 NYMC X-179A and B/Brisbane/60/2008 (IOAM treated or untreated), or diluent only control. Immunizations were delivered on day 0 and day 21 in a total volume of 100 µl via the intramuscular route of administration (50 µl/caudal thigh muscle). Blood samples were collected by retro-orbital bleed on day −2 (pre-bleed), day 21 (pre-boost) and by cardiac puncture on day 42 (post-boost). Sera was separated and stored at −20° C. for determination of hemagglutination inhibition (HAI) assay titer. Statistical analysis was performed using JMP software (SAS software, Inc.). In another experiment, 7-8 week-old, female BALB/c mice (Charles River) were immunized with 12, 6.0, 3.0, 1.5, 0.75, 0.38, or 0.19 ug of HA/strain (determined by SRID potency assay) of each trivalent (TIV) or quadrivalent (QIV) formulated bulk drug product containing all 4 (QIV) or a combination of 3 (TIV)influenza strains (IOAM treated or untreated): A/California/07/2009 NYMC X-179A (A/Cal), A/Texas/50/2012 X223A (A/Tex), B/Brisbane/60/2008 (B/Bris) and B/Massachusetts/02/2012, or diluent only control. Similarly, immunizations were delivered on day 0 and day 21 in a total volume of 100 µl via the intramuscular route of administration (50 µl caudal thigh muscle). Blood samples were collected by retro-orbital bleed on day −2 or −1 (pre-bleed), day 20 (pre-boost) and by cardiac puncture on day 35 (post-boost). Sera was separated and stored at −20° C. for determination of HAI titer. Statistical analysis was performed using SAS® Version 9.2 software (SAS software, Inc.).

Figure 13:
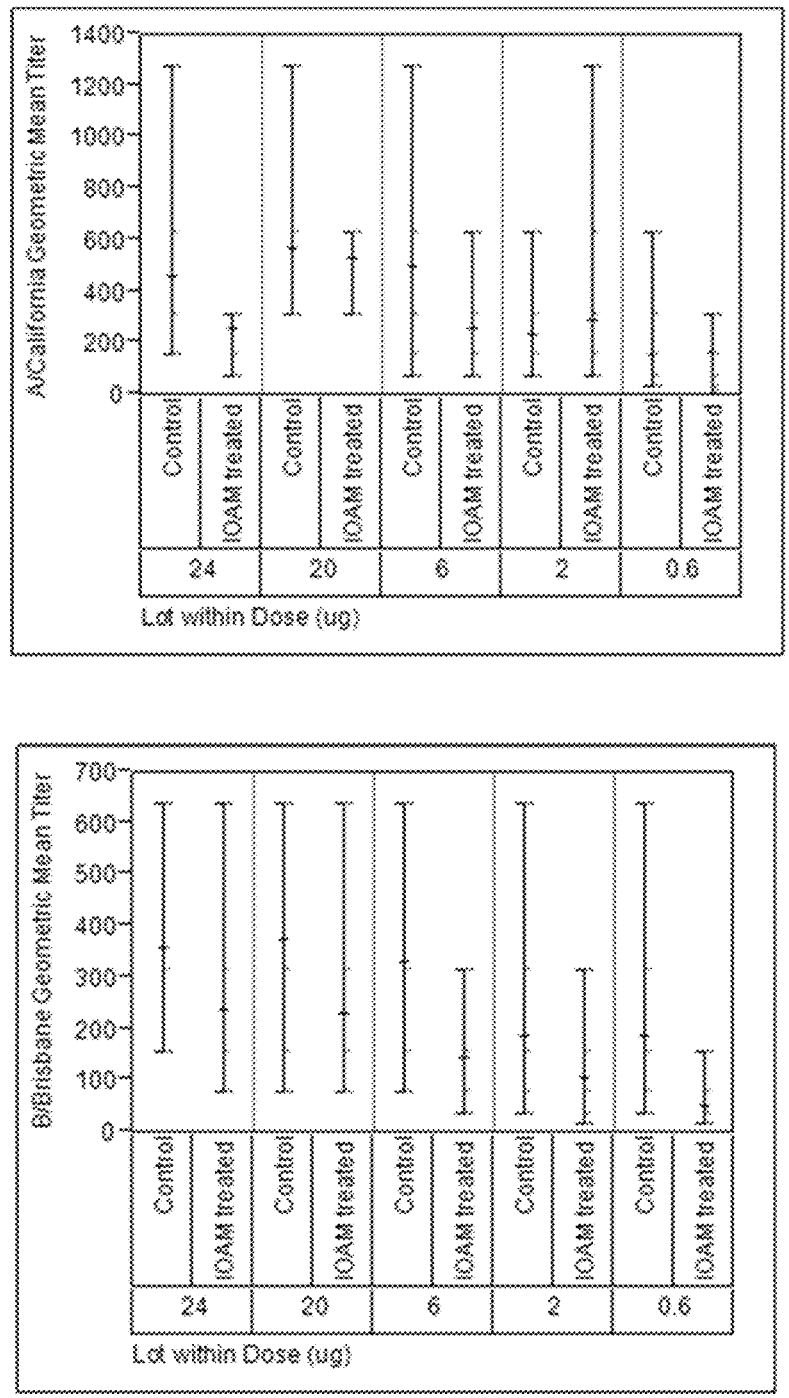
FIG. 13 depicts exemplary data illustrating that influenza vaccines containing HA antigens treated with IOAM generally demonstrated at least comparable immunogenicity in a mouse model as compared to control vaccines without the treatment of IOAM.

Exemplary data are shown in FIG. 13. As can be seen, influenza vaccines containing HA antigens treated with IOAM generally demonstrated at least comparable immunogenicity as compared to control vaccines without the treatment of IOAM.

Additional immunological and product characterization studies on IOAM treated vaccine samples can also be performed. For example, identification of the alkylation sites impacted are investigated using an LC/MS peptide mapping method. Additionally, a survey of the epitope binding for the control sample versus the IOAM treated samples using Biacore technology can be studied employing antibodies associated with protection.

Example 7

Alkylation Treatment does not Affect Immunogenicity

This example demonstrates that treatment with an alkylating agent (e.g., IOAM) does not alter immunogenicity. The effect of alkylation of influenza vaccines containing HA antigens was analyzed in a mouse model for B/Brisbane/60/2008 & A/Texas/50/2012. Formulations at different Triton:HA ratios were tested in 8 week-old, female, BALB/c mice (n=15 mice/group). Doses (100 µL) were prepared and administered on D(day) 0 and D21. Sera was collected on D35.

Figure 14:
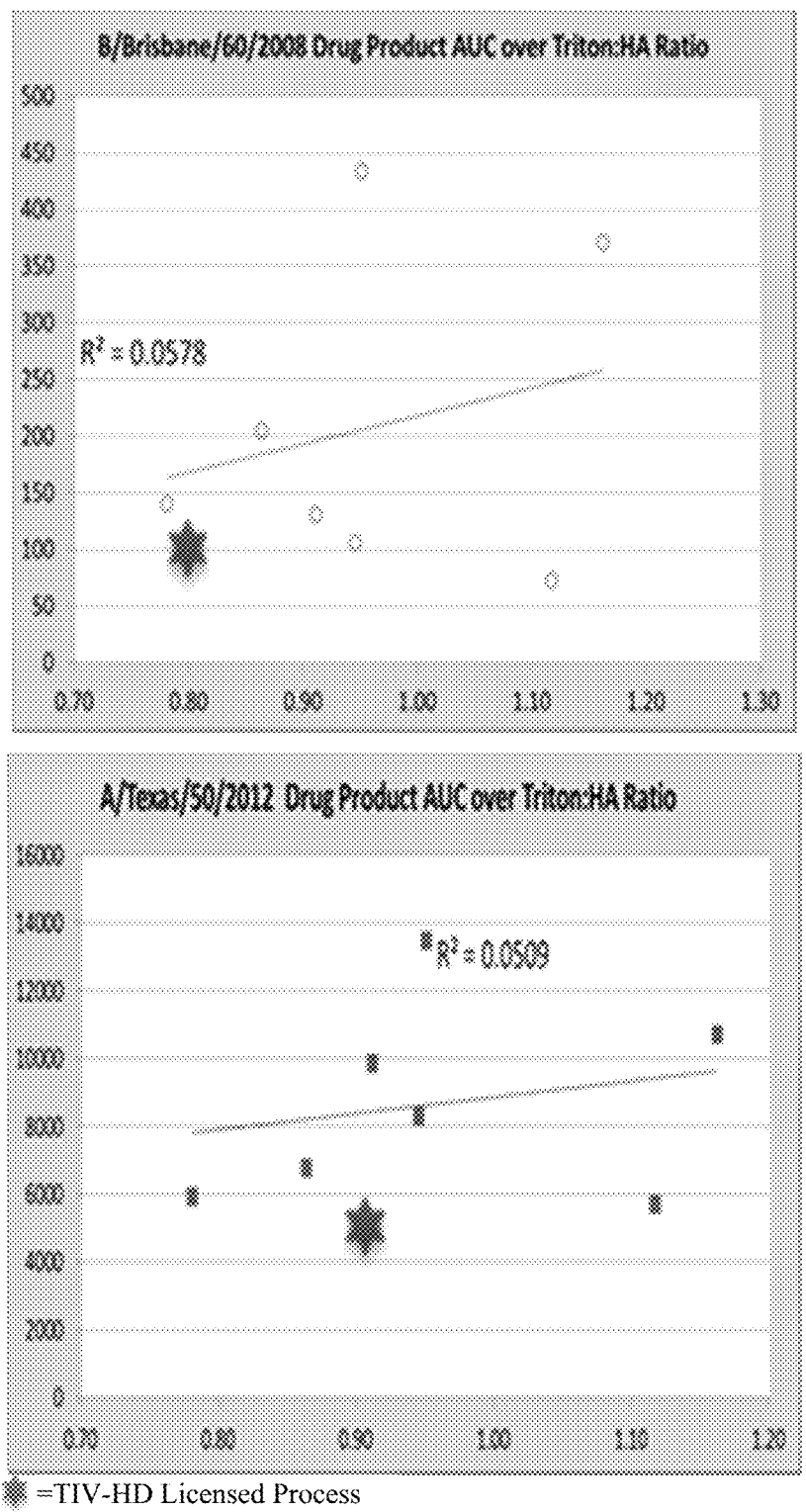
FIG. 14 depicts exemplary data illustrating that influenza vaccines containing HA antigens treated with IOAM generally demonstrated HAI assay titer AUC responses similar to HA antigens prepared without IOAM with the TIV-HD process.

The hemagglutination inhibition (HAI) assay, a functional assay for the determination of influenza virus neutralizing antibody titer, was used to determine the immunogenicity of influenza virus vaccines. Area under the curve (AUC) of the HAI assay titers across the dose range was calculated using the Bailer method for each formulation. FIG. 14 illustrates the AUC responses of alkylated hemagglutinin are comparable to the currently licensed high dose trivalent inactivated influenza vaccine (TIV-HD). The X axis represents Triton:HA ratio. The Y axis represents the AUC (Area under the Curve) generated from the dose response curve for each formulation. These results indicate that alkylation treatment does not affect immunogenicity.

EQUIVALANTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

In the claims articles such as "a", "an" and "the" may mean one or more than one unless indicated to the contrary or otherwise evident from the context. Thus, for example, reference to "an antibody" includes a plurality of such antibodies, and reference to "the cell" includes reference to one or more cells known to those skilled in the art, and so forth. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are presenting, employed in, or otherwise relevant to a given product or process. Furthermore, it is to be understood that the invention encompasses all variations, combinations, and permutations in which one or more limitation, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for anyone of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understand of one of ordinary skill in the art, values that are expressed as ranges can assume any specific value or sub-range within the state ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

We claim:

1. An influenza vaccine comprising a hemagglutinin treated with an alkylating agent, wherein the influenza vaccine is substantially free of alkylating agent and retains at least about 90% potency as determined by Single Radial Immunodiffusion (SRID) assay upon storage of about 6 months at a temperature ranging from 1-30° C.

2. The influenza vaccine of claim 1, wherein the hemagglutinin contains 1-5, 1-4, 1-3 or 1-2 alkylated cysteine residues.

3. The influenza vaccine of claim 1, wherein the hemagglutinin contains one or more alkylated cysteine residues, wherein the one or more alkylated cysteine residues constitute about 1-50%, 1-40%, 1-30%, 1-20% or 1-10% of total cysteine residues present in the hemagglutinin.

4. The influenza vaccine of claim 1, wherein substantially all cysteine residues with free sulfhydryl groups are alkylated.

5. The influenza vaccine of claim 1, wherein the hemagglutinin treated with an alkylating agent comprises methylated cysteine residues.

6. The influenza vaccine of claim 1, wherein the alkylating agent is selected from the group consisting of 2-iodoacetamide (IOAM), iodoacetic acid, 2-bromoacetamide, glutathione bromoacetamide, bromoacetic acid, 1,3-propane sultone, methyl methanethiosulfonate, methoxycarbonylmethyl disulfide, maleamide, maleimide-PEG, vinylpyridine, N-ethylmaleimide, tosylacetamide, and combination thereof.

7. The influenza vaccine of claim 1, wherein the vaccine is a split influenza virus vaccine.

8. The influenza vaccine of claim 1, wherein the influenza vaccine is a recombinant influenza vaccine.

9. The influenza vaccine of claim 1, wherein the influenza vaccine is an egg based influenza vaccine.

10. The influenza vaccine of claim 1, wherein the influenza vaccine is produced in insect cells, mammalian cells, yeast cells, viral cells, fungus or algae.

11. The influenza vaccine of claim 1, wherein the influenza vaccine is a monovalent, divalent, trivalent or quadrivalent influenza vaccine.

12. The influenza vaccine of claim 1, wherein the storage temperature ranges from 2-10° C.

13. The influenza vaccine of claim 6, wherein the alkylating agent is 2-iodoacetamide (IOAM).

* * * * *